United States Patent [19]
Laine et al.

[11] Patent Number: 5,648,610
[45] Date of Patent: Jul. 15, 1997

[54] METHOD AND APPARATUS FOR THE CHARACTERIZATION AND CONTROL OF POWDER COMPACTION

[76] Inventors: Ensio Laine, Allinpolku 5., FIN-21290 Rusko; Harry Jalonen, Hurtinkatu 11 A 4, FIN-20610 Turku; Arvi Hakanen, Västäräkinpolku 3 C 82, FIN-20610 Turku; Kari Linsaari, Talpiankuja 6 as 12, FIN-20610 Turku; Juha Jokinen, Jalustinkatu 7 A 1, FIN-20880 Turku, all of Finland

[21] Appl. No.: 424,350

[22] PCT Filed: Nov. 9, 1993

[86] PCT No.: PCT/FI93/00462

§ 371 Date: May 25, 1995

§ 102(e) Date: May 25, 1995

[87] PCT Pub. No.: WO94/11731

PCT Pub. Date: May 26, 1994

[30] Foreign Application Priority Data

Nov. 13, 1992 [FI] Finland ................... 925158

[51] Int. Cl.$^6$ .................................................. G01H 11/00
[52] U.S. Cl. .................................................. 73/587; 73/801
[58] Field of Search ........................... 73/579, 587, 595, 73/790, 801, 813, 602; 364/551.01, 555, 506, 508

[56] References Cited

U.S. PATENT DOCUMENTS

| | | | |
|---|---|---|---|
| 3,946,600 | 3/1976 | Rettig | 73/587 |
| 4,494,408 | 1/1985 | DeLacy | 73/587 |
| 4,501,149 | 2/1985 | Konno | 73/587 |
| 4,959,638 | 9/1990 | Palmer | 73/587 |
| 5,052,215 | 10/1991 | Lewis | 73/40.5 A |
| 5,140,858 | 8/1992 | Nishimoto | 73/587 |
| 5,172,597 | 12/1992 | Hedeen | 73/602 |

FOREIGN PATENT DOCUMENTS

| | | |
|---|---|---|
| 0 309 155 A2 | 3/1989 | European Pat. Off. . |
| 0 317 322 A2 | 5/1989 | European Pat. Off. . |
| 0 347 303 A2 | 12/1989 | European Pat. Off. . |
| WO90/02944 | 3/1990 | WIPO . |
| WO91/10904 | 7/1991 | WIPO . |

OTHER PUBLICATIONS

Derwent's Abstract No. 89-213103/29, Week 8929, SU, A2, 1453314 Jan. 23, 1989.
International Journal of Pharmaceutics, pp. 29-36, vol. 36, 1987, M.J. Waring et al., "Acoustic Emission of Pharmaceutical Materials During Compression". (No month).

Primary Examiner—Christine K. Oda
Attorney, Agent, or Firm—Kubovcik & Kubovcik

[57] ABSTRACT

A method and device for characterizing the compaction result of a powder and monitoring the compaction of the powder during the compaction process. In the method sound emission produced by the compaction process is measured by a sensor and transformed into a frequency spectrum in which the sound intensity is presented as a function of frequency. The intensity of the band relating to the sound emission arising from the compaction of the powder is recorded using different compressive forces, and the compaction result is obtained as a function of the intensity of the band relating to the sound emission arising from compaction. The device includes a roller compactor, a microphone disposed proximate to the roller compactor, an amplifier connected to the microphone, an analog/digital converter connected to the amplifier, a frequency analyzer connected to the converter, a monitor connected to the analyzer, a regulator for detecting deviation between a value from the monitor and a set value from a standard spectrum and generating a control signal on the basis of the detected deviation, and an actuator for adjusting the roller compactor to vary the compressive force applied to the powder during compaction, the actuator being activated by the control signal generated by the regulator.

10 Claims, 28 Drawing Sheets

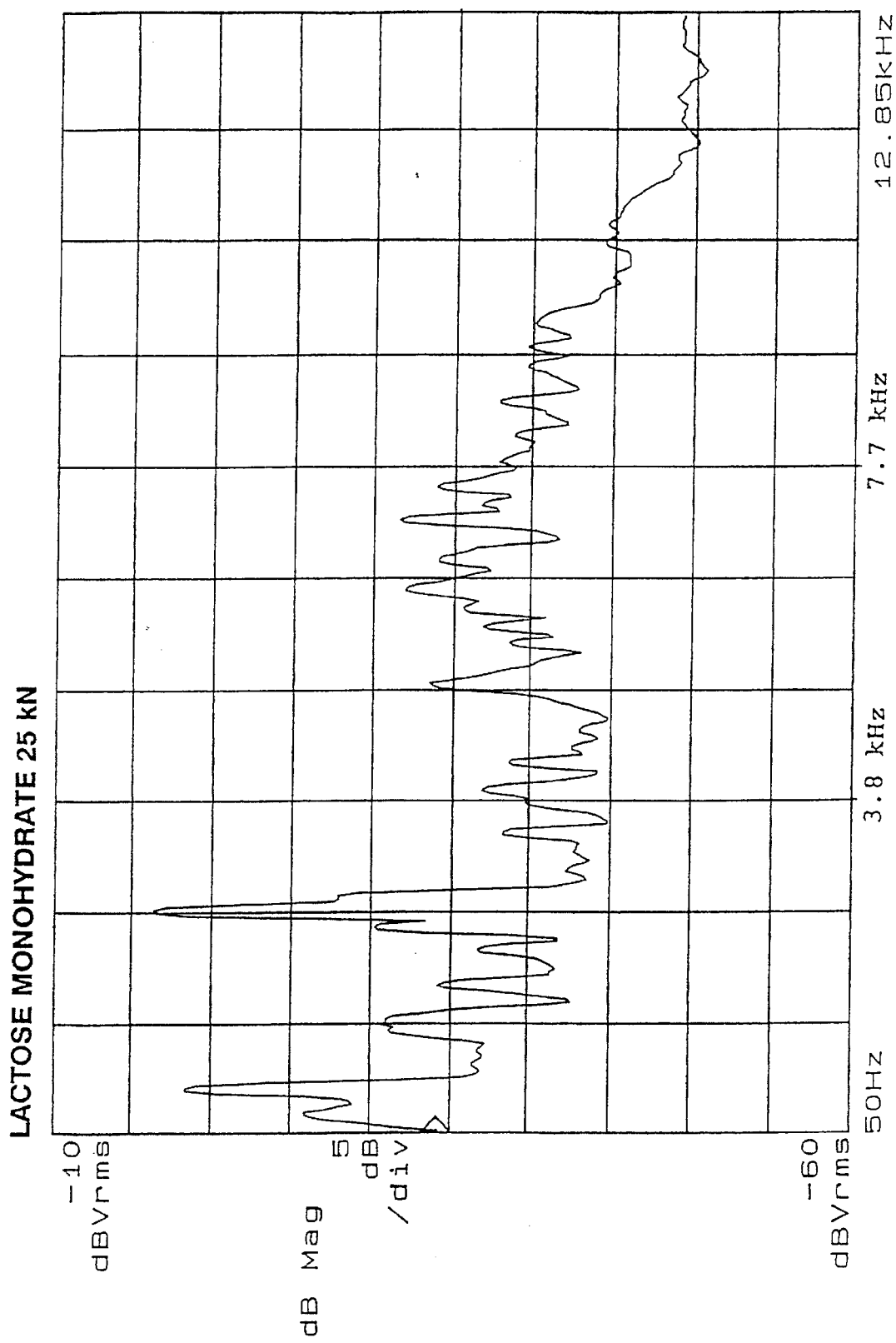

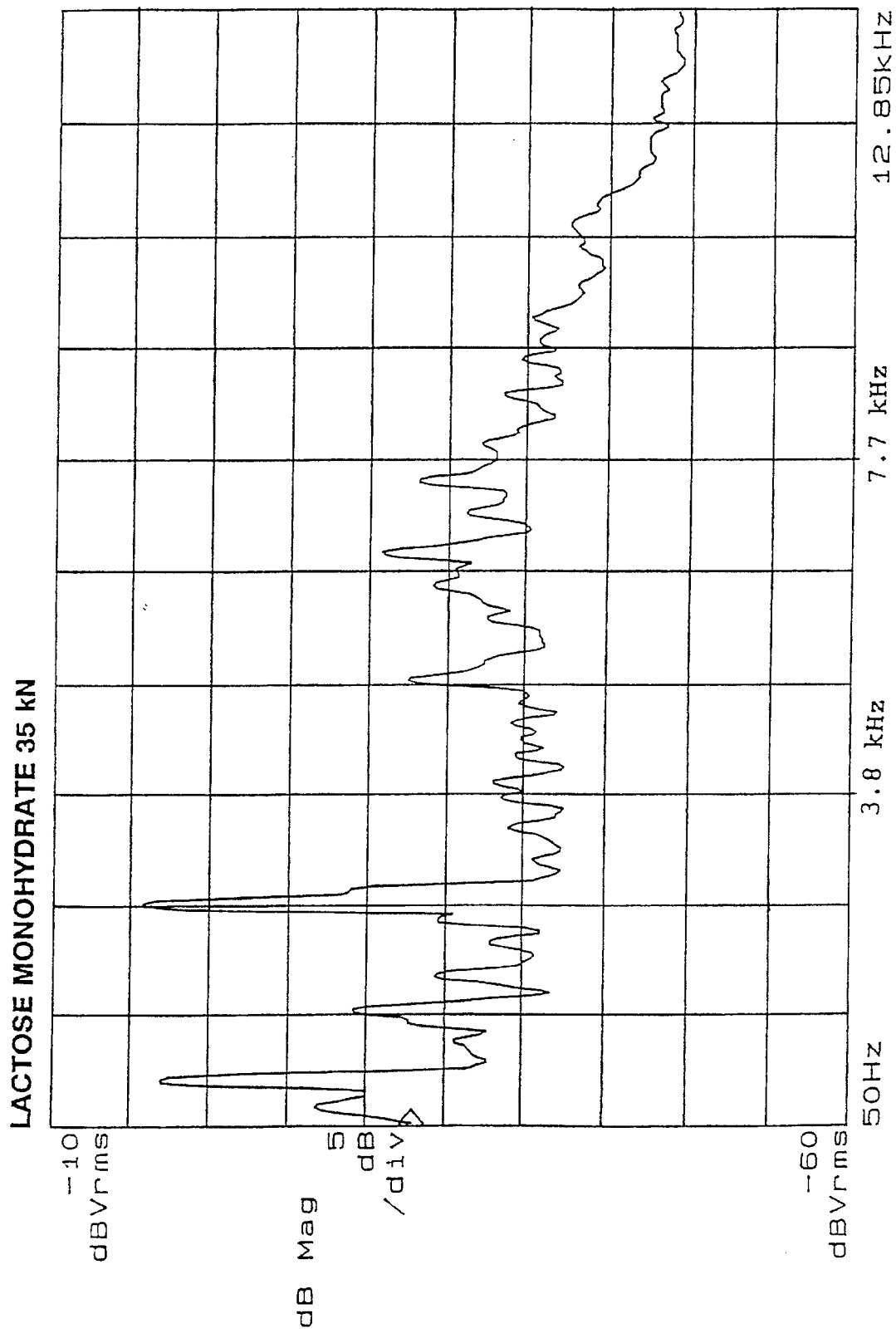

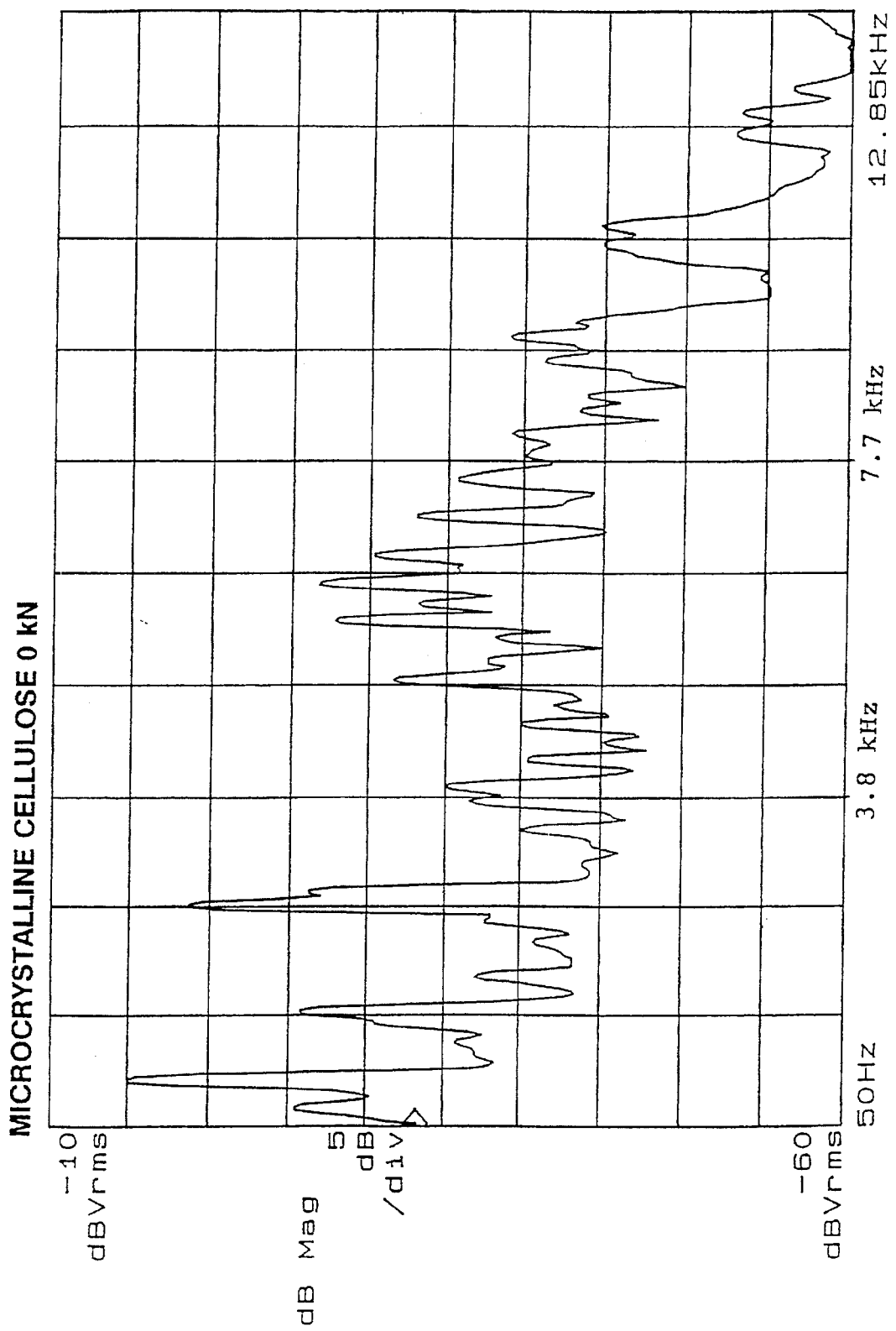

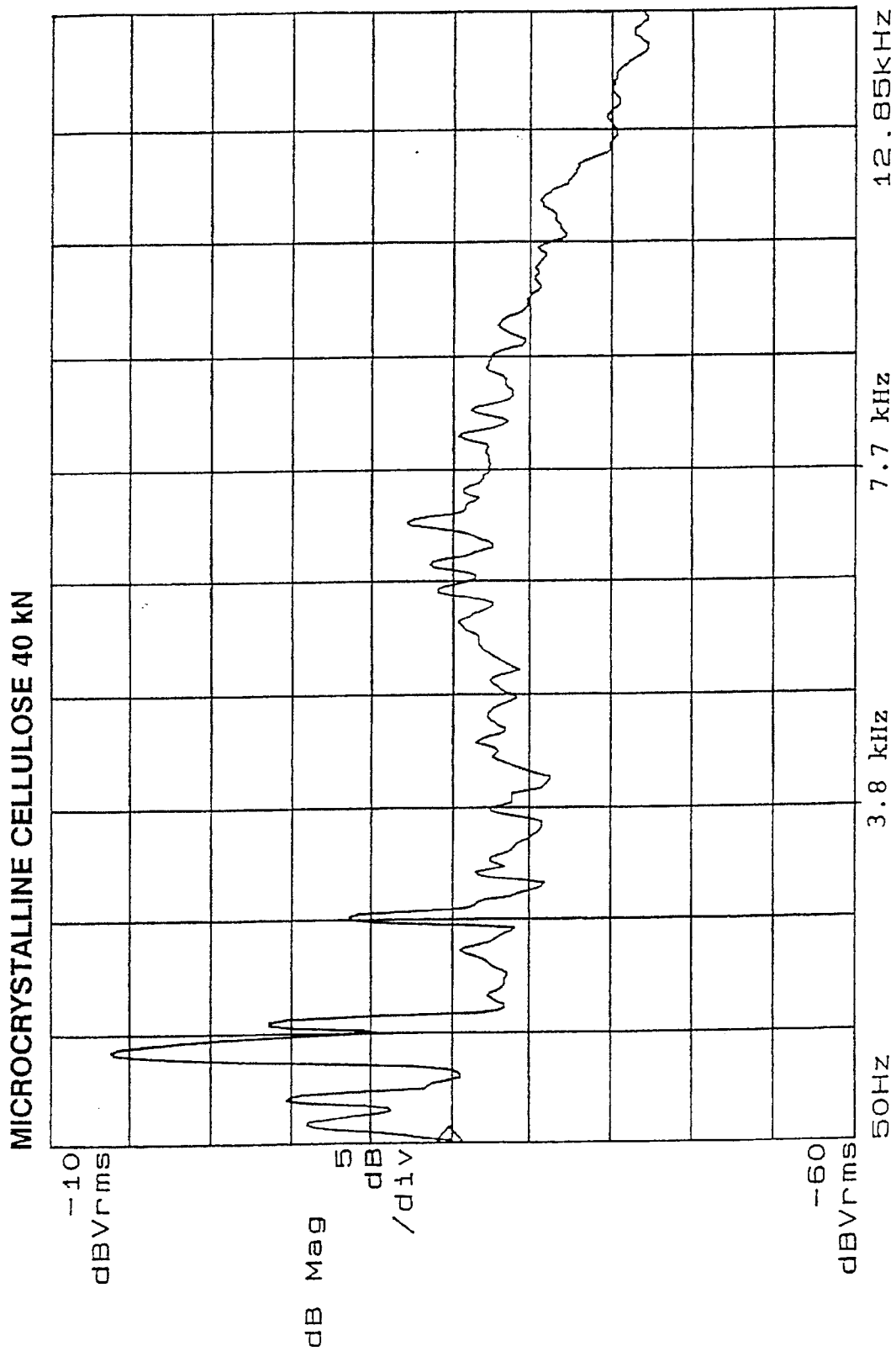

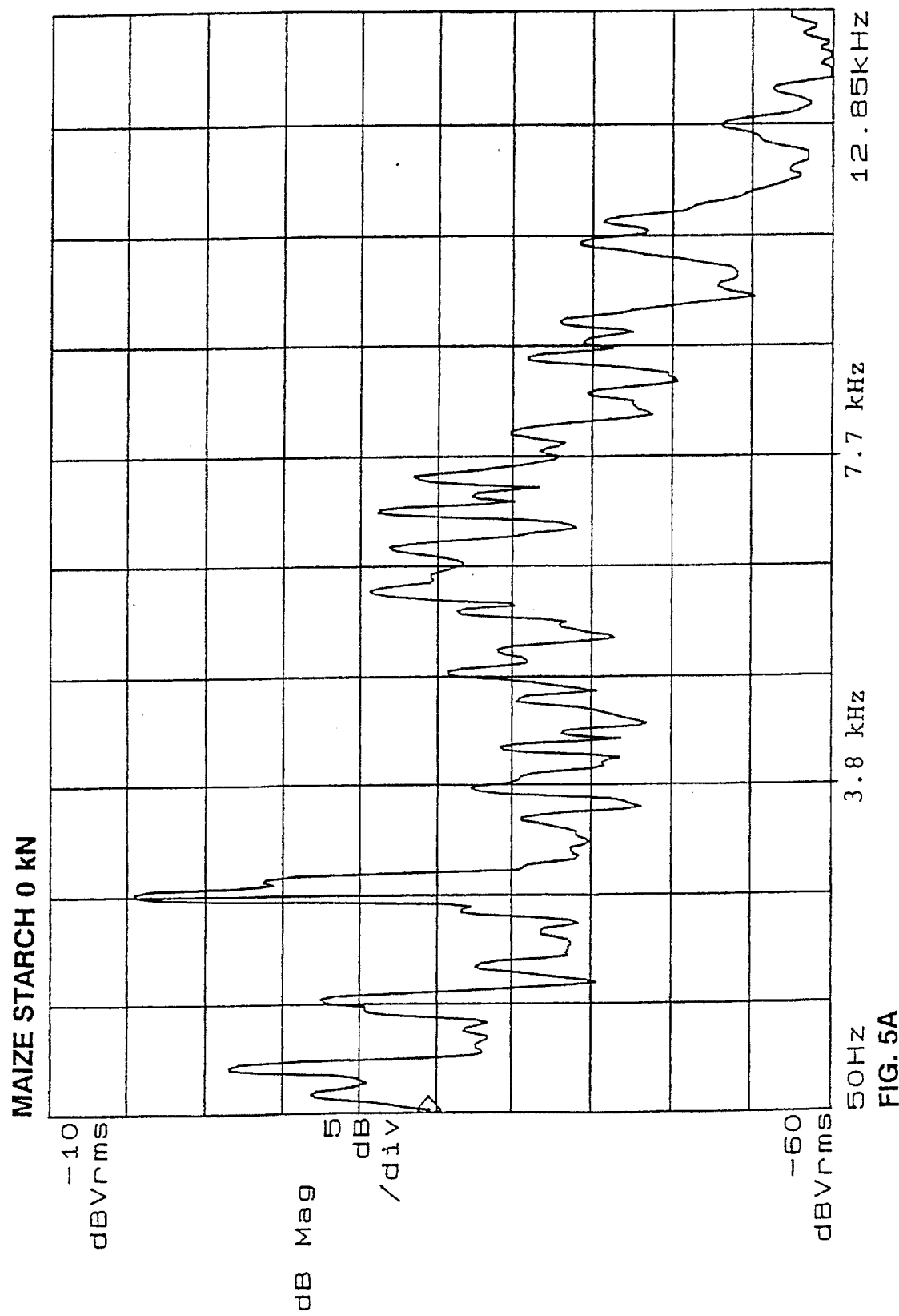

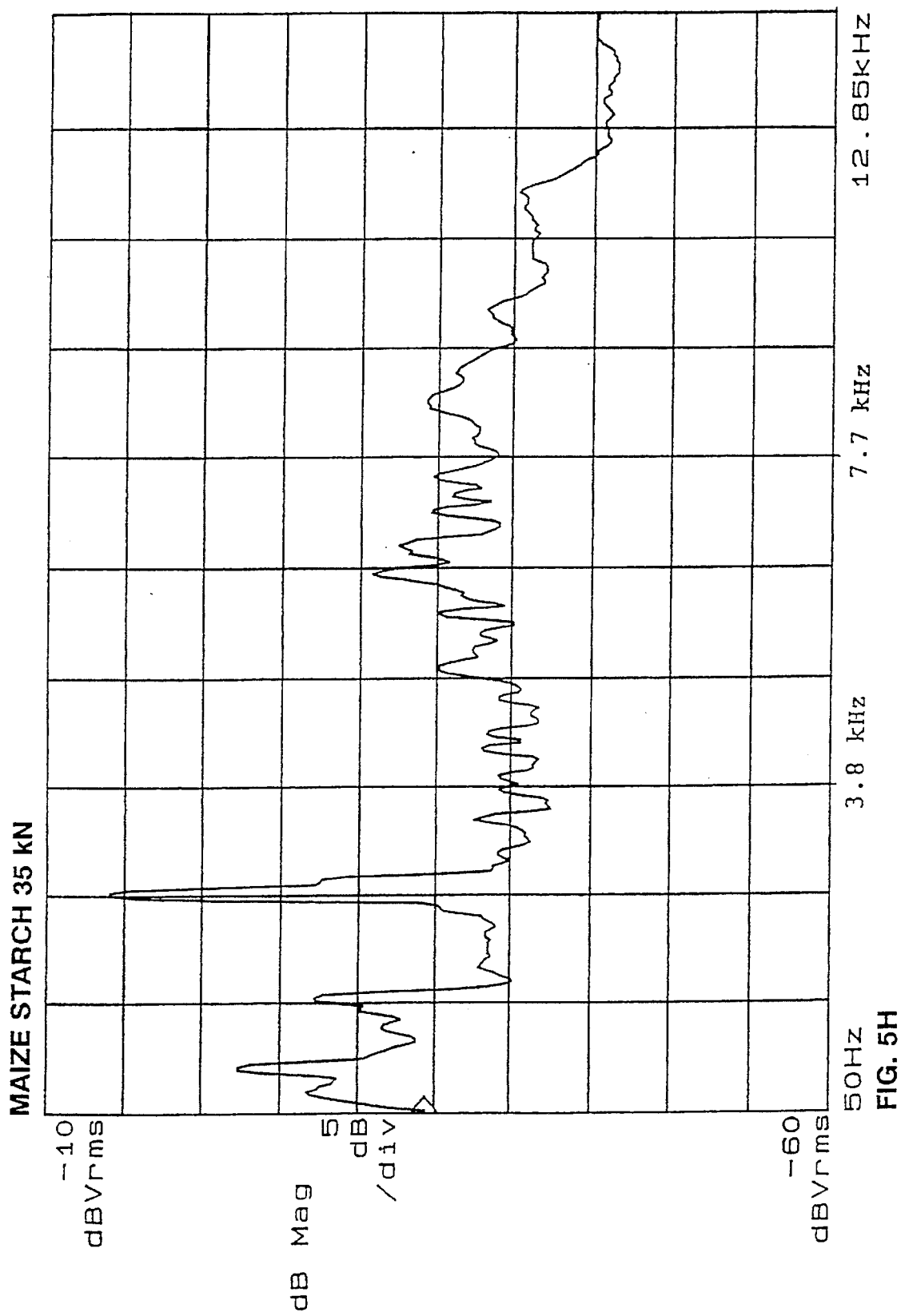

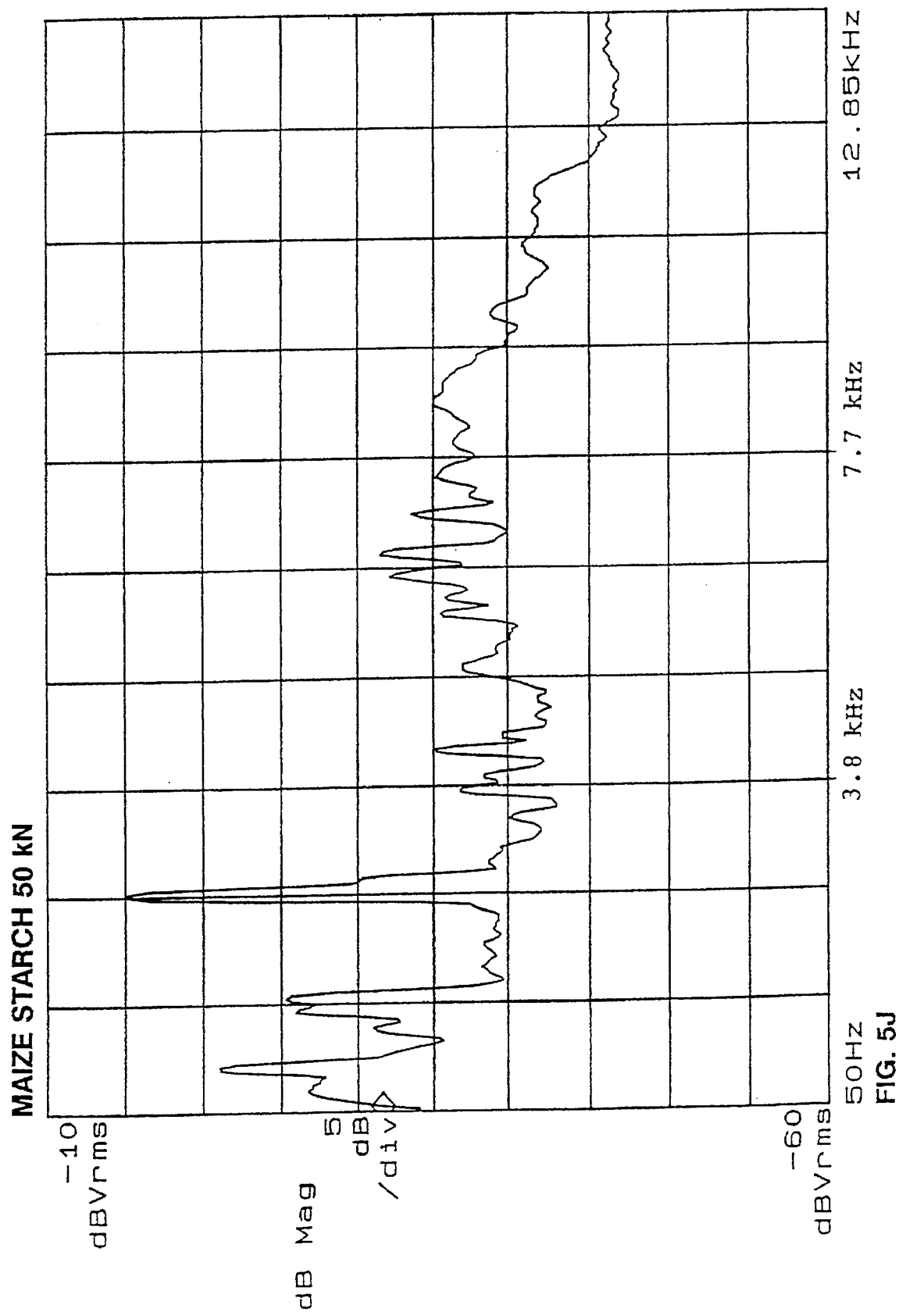

METHOD AND APPARATUS FOR THE CHARACTERIZATION AND CONTROL OF POWDER COMPACTION

FIELD OF THE INVENTION

The invention relates to a method for characterizing the compaction of powder materials acoustic emission occurring during compaction of said materials, and a device for examining the compressibility of powder materials and monitoring the compaction process.

BACKGROUND OF THE INVENTION

Compaction means compressing powdery materials to greater density and smaller volume. Compaction is a common material-technological procedure in many fields of technology, particularly in metallurgy and ceramics. Compaction usually precedes a further phase, such as sintering.

In the pharmaceutical industry, compaction is used especially in making granules, particularly in dry granulation, when granules are made from moisture-sensitive materials. The pieces made during compaction are broken down into granules of desired shapes and sizes. Granulation, on the other hand, is one of the most important part processes of tabletting in pharmaceutical technology. Roughly speaking, granulation methods can be divided into wet and dry methods, depending on whether liquid is added to the powder mass or not. The purpose of granulation is to produce, from the powder, granules of appropriate size and strength in the shape of grains or balls. More broadly speaking, granulation means enlarging the size of powder particles. In granulating powders or powder compounds the aim is, for example, to improve the flow and distribution accuracy of the mass, reduce dusting, improve binding when compressing tablets, reduce separation of components, and accomplish a certain microstructure for the compacted powder.

Compaction is usually carried out as a batch process, but can also be performed as a continuous process, for example, by means of a roller compactor. Compaction can be carried out at room temperature or at an elevated temperature. The pressures used normally vary within the range of 70–700 MPa.

The properties most closely related to the behavior of the powder being compacted are the compressibility and green strength of the piece. Compressibility is an indicator of the change in density obtainable through compaction. Green strength is an indicator of the cohesion of the compacted piece.

A common problem of compaction processes is that the powder to be compacted does not become compressed in the expected manner. Especially where the compacted product is to be further worked into granules, it is a considerable disadvantage if loose powder has remained inside the compacted product, because this produces reject in the granulation process. If, on the other hand, the product to be compacted should remain in one piece as it is, for example, for the purpose of sintering or some other work phase, it is extremely disadvantageous if the compacted product splits during the compaction process.

One reason for the compaction problems is that the wrong compressing pressure has been selected with respect to those properties of the powder to be compacted that have an effect on compressibility. The most important properties affecting the compressibility of an organic powder are the capability of the powder to form van der Waals' bonds, particle size and shape, and particle size distribution. The appropriate compression pressure is dependent mainly on these properties. Different powder types are examined on laboratory and pilot scale, in an attempt to find the suitable compression pressure for each powder and powder compound type, with a view to the production process. In practice it has, however, been found that selecting the compression pressure merely on the basis of these parameters will not give a satisfactory compaction result. Thus, in practice, extensive series of test compressions have to be made with the powder or powder compound to be compacted in order to find the suitable compression pressure for the production process. Preparing such test batches is obviously laborious and very slow.

The aim of the present invention is to eliminate the above problems and to present a new method and device for monitoring the compressibility of a powder being compacted during the compaction process, and possibly for controlling the compaction process. The invention is based on the observation that acoustic emission gives a good indication of compressibility and thus the invention is based on analyzing the acoustic emission produced during the compaction process. If the powder is an organic substance, or a compound of organic substances, the acoustic emission arising from compressibility occurs at least for the most part in the audible region.

On the basis of the publication M J Waring et al, Int. J Pharmaceutics, 36 (1987) 29–36 it is known that the compressibility properties of pharmaceutical powders can be deduced on the basis of acoustic emission. Compressing has been studied in connection with tabletting by measuring the total amplitude of the acoustic emission as a function of time in the ultrasonic region. The publication does not analyze the spectrum of acoustic emission, and thus does not give any suggestions as to how the observation made could be utilised to control the compaction process.

Patent Publication No. 0 347 303 discloses the examination of the compaction of uranium pellets by means of a piezoelectric sensor, in which case the acoustic emission signal appears in the ultrasonic region. The occurrence and spreading of compression errors can be followed as a function of time on an amplitude curve. The spectrum of the acoustic emission has not been analyzed in this publication either.

Therefore, it has not previously been disclosed how the compaction process could be monitored and controlled on the basis of acoustic emission. A study of the literature did not bring forward any mention at all of measuring acoustic emission occurring in the audible region in connection with studies on the compressing properties of materials being compacted.

The compaction of organic substances is based on the fact that van der Waals' forces may cause binding between powder particles, the distance between which is smaller than 1000Å. Binding improves if the number of connection points between the powder particles increases.

Friction work together with possible powder particle fractures give rise to acoustic emission when powder is compressed. The sounds are produced mainly in the audible region if organic substances are in question. The general properties of the substance, such as the ability to form van der Waals' bonds, and the specific properties of the substance batch in question, such as particle shape and size and particle size distribution, are the most significant parameters affecting compressibility.

SUMMARY OF THE INVENTION

The invention thus relates to a method for characterizing the compaction result of a powder, especially compressibility, during the process. According to the invention, a) sound emission produced by the process is measured by means of a sensor located in the vicinity of the process and transformed into a frequency spectrum in which sound intensity is presented as a function of frequency, and b) the intensity of the frequency band relating to the sound emission arising from the compaction of the powder is recorded and integrated, using a certain compressive strength, and the compaction result obtained is noted. The steps a) and b) are repeated changing the compressive force, which thus gives the compaction result as a function of the intensity of the frequency band relating to the sound emission produced by compaction.

The invention also comprises a method for monitoring the act of compaction of powder during the process, in which case the act of compaction depends at least on the compressibility of the powder and the functioning of the compaction equipment. The sound emission produced by the process is measured by means of a sensor located in the vicinity of the process and transformed into a frequency spectrum in which sound intensity is shown as a function of frequency, and the intensity of the frequency band relating to the sound emission arising from the compaction of the powder is recorded and possibly integrated, and the sound intensity of the frequency band relating to the compaction of the powder is compared with the corresponding sound intensity of the standard spectrum of the powder being compacted, which is used as the normative value, and the deviation is recorded. If desired, the intensity of the frequency band relating to the sound emission caused by the compaction equipment is recorded and integrated, and the sound intensity of the frequency band relating to the functioning of the compaction equipment is compared with the corresponding sound intensity of the standard spectrum, which is used as the normative value, and the deviation is recorded.

The invention also comprises the device used in the method described above, which includes a microphone connected in the vicinity of the process, an amplifier, an analog/digital converter, a frequency analyzer, and a monitor.

According to one embodiment of the invention, the compressive force of the compaction process is automatically controlled on the basis of the recorded deviation. The aim is to maximize the sound intensity relating to the most suitable compression properties by regulating the force.

According to another embodiment of the invention, the sound emission arising from the compressibility of the powder is measured within the audible region. This suits organic substances well, as their particles are relatively soft.

The method relating to the invention is carried out by first producing, on laboratory or pilot scale, acoustic spectra of the powder type to be compacted using compressive forces of different magnitudes. The spectrum relating to the most suitable compression properties is selected as the standard spectrum for controlling the process. By aiming in process control at the same frequency intensity spectrum in some respects, good compressibility results are achieved, even if the particle shapes and sizes in the powder batch being compacted vary.

In searching for the standard spectrum, it should be noted by powder type whether the sound intensities higher or lower than the standard intensity are due to the compressive force being too strong or too weak, as such a deviation is extremely dependent on powder type. With some powder types, a sound intensity lower than the standard intensity may be a sign of the compressive force having been too strong and the powder has, for example, fused. In connection with another powder type on the other hand, a too low a sound intensity in comparison with the standard intensity may be a sign of the compressive force having been insufficient. When these aspects are analyzed by powder type, it can also be deduced in which direction the compressive force must be changed during the process, if the process is to be controlled automatically by means of a sound intensity spectrum.

The method relating to the invention is applicable to all types of powders and different types of processes, that is, both to batch compaction and continuous compaction.

The following tests, which describe acoustic measurements during the compaction of different materials, illustrate the usefulness of the invention.

Acoustic emission was measured during the compaction of three different pharmaceutical auxiliary substances: crystalline lactose monohydrate, microcrystalline cellulose and amorphous maize starch, with compressive forces varying within the range 0–60 kN. The acoustic emission signals were recorded by microphone on magnetic tape and transformed into frequency spectra by using FFT analysis (Fast Fourier Transformation). After rough identification of the peaks appearing in different frequency bands, each spectrum was divided into three bands. By calculating the total acoustic power of the different bands, that is, by integrating the sound intensity of different frequency bands, the acoustic activity of the different bands could be compared quantitatively.

The auxiliary substances studied, lactose monohydrate (De Melkindustrie Veghel B.V., Veghel, Holland), microcrystalline cellulose (Edward Mendell Finland Oy, Nastola, Finland), and maize starch (Cerestar Scandinavia A/S, Holte, Denmark) were compacted with compressive forces within the range 0–60 kN. The crystal size of the microcrystalline cellulose was 50 µm and it was the only one of the substances studied which actually became compacted. The value 0 kN describes a situation where the compactor rolled small amounts of material without any compressive force. In the compaction of lactose monohydrate, greater compressive forces than 35 kN could not be used as the material then became sticky.

The materials were compacted by means of a Bepex Pharmapaktor 200/50 P roller compactor. Corrugate-profiled rollers were used for each study. In this machine type the axles of both rotating rollers are solidly supported. In the compaction process, the rollers are thus in practice radially inelastic. The space between the rollers is kept constant. Thus the force acting transversely on the rollers and arising from the material being compacted between the rollers can be used as the measure of compressive force.

The compressive force is regulated by changing the feed flow of the material being compacted. The feed flow can be regulated by changing the rotating speed of the feeder-compression screw of the compaction device, while the speed of rotation of the rollers is kept constant. This is important for the acoustic emission measurements. The sound produced by the rollers is thus constant, and therefore easier to distinguish from the sound produced by the material being compacted. In the tests the speed of the rollers was 6 rpm.

The rotating speed of the feeder-compression screw is adjusted automatically by means of an adjustment device connected to the compressive force measuring gauge. The force signal is monitored continuously, and it incorporates feedback to the feeder-compression screw. The compressive force can be read on a digital display. During the tests, the compressive force was allowed to stabilize, before measurements were started. The force signal could also be recorded during compaction to analyze its stability.

To detect acoustic emission, an omnidirectional electret condenser microphone with a frequency sensivity band of approximately 50 Hz–13 kHz was used. The microphone, protected from dust by a foamed plastic hood, was placed on a tripod about 10 cm away from the compactor rollers. The signals were recorded by means of a battery-operated preamplifier and a deck on cassette tape, from where they were then transferred for analysis to a frequency analyzer capable of measuring frequencies within the range from 0–100 kHz. The spectra obtained were recorded on computer discs.

Acoustic signals were generally recorded at 5 kN intervals, for two minutes at a time. The analyser takes 500 samples from such a signal, and on the basis of them calculates an average spectrum by means of the FFT-program. In the spectra, the X axis shows frequency in the region from 50 Hz to 12.85 kHz and the Y axis shows intensity level L of the sound. The scale is from −60 to −10 $dBV_{rms}$.

L can be calculated from the formula $$L[dBV_{rms}] = 20 \log(U/U_o),$$

in which $U[V_{rms}]$ is the signal voltage and $U_o$ is the reference voltage, or 1 $V_{rms}$, which is the maximum signal voltage. The abbreviation rms stands for 'root mean square'.

The sensivity of the microphone was −66 $dBV_{rms}$ ±3 $dBV_{rms}$. The shape of the sensitivity curve of the microphone had a general effect on the shape of the spectra.

The spectra can be analyzed by calculating the total power of acoustic emission in a given frequency band. The unit of this power is the same as that of the intensity level which is itself a power comparable to the square of the voltage. The general shape of the spectra is partly due to the sensitivity curve of the microphone.

Integrated intensity was obtained by calculating the area of the intensity peak in the intensity-frequency spectrum. Calculating the integrated value is useful for making quantitative comparison possible. The Y axis of descriptors 3, 4 and 5 (FIGS. 3A–3F, 4A–4I and 5A–5K) is the intensity level [dB] comparable to the logarithm of intensity, in which case the visual observation does not correspond to the true area of the peak. The computer, therefore, calculates the intensity but transforms it into dB units. Integration was carried out by the following formulae:

$$L[dB] = 20 \log (U/U_o),$$

from which it follows that $$[B]L = 2\log(U/U_o) = \log (U/U_o)^2 = \log I/I_o$$

$$\int_{f_1}^{f_2} L df = \log \int_{f_1}^{f_2} (I/I_o) df = \log \int_{f_1}^{f_2} (U^2/U_o^2) df = \log \sum_{f_1}^{f_2} (U/U_o)^2$$

($f$ = frequency)

BRIEF DESCRIPTION OF THE DRAWINGS

FIGS. 3A–3F show the frequency intensity spectra of lactose monohydrate with different compressive forces.

FIGS. 4A–4I show the frequency intensity spectra of microcrystalline cellulose with different compressive forces.

FIGS. 5A–5K show the frequency intensity spectra of maize starch with different compressive forces.

DESCRIPTION OF THE PREFERRED EMBODIMENTS

Figure 1:
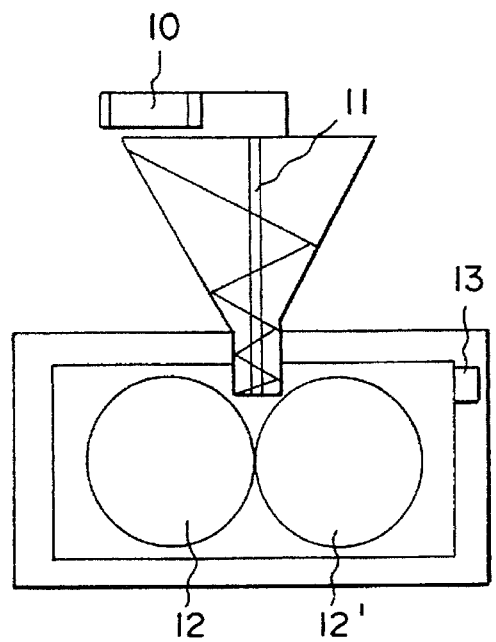
FIG. 1 shows the main features of the roller compactor used to compact powder materials.

In FIG. 1, which shows the roller compactor, reference number 10 refers to the motor of the feeder-compression screw 11. The axles of rollers 12 and 12' are solidly supported. Reference number 13 refers to the compressive force measuring gauge.

Figure 2:
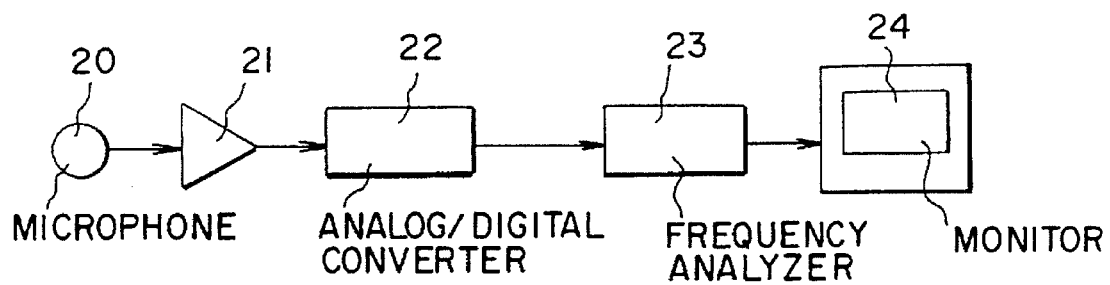
FIG. 2 shows the main features of the device used for the recording and further handling of the sound emission.
Figure 3A:
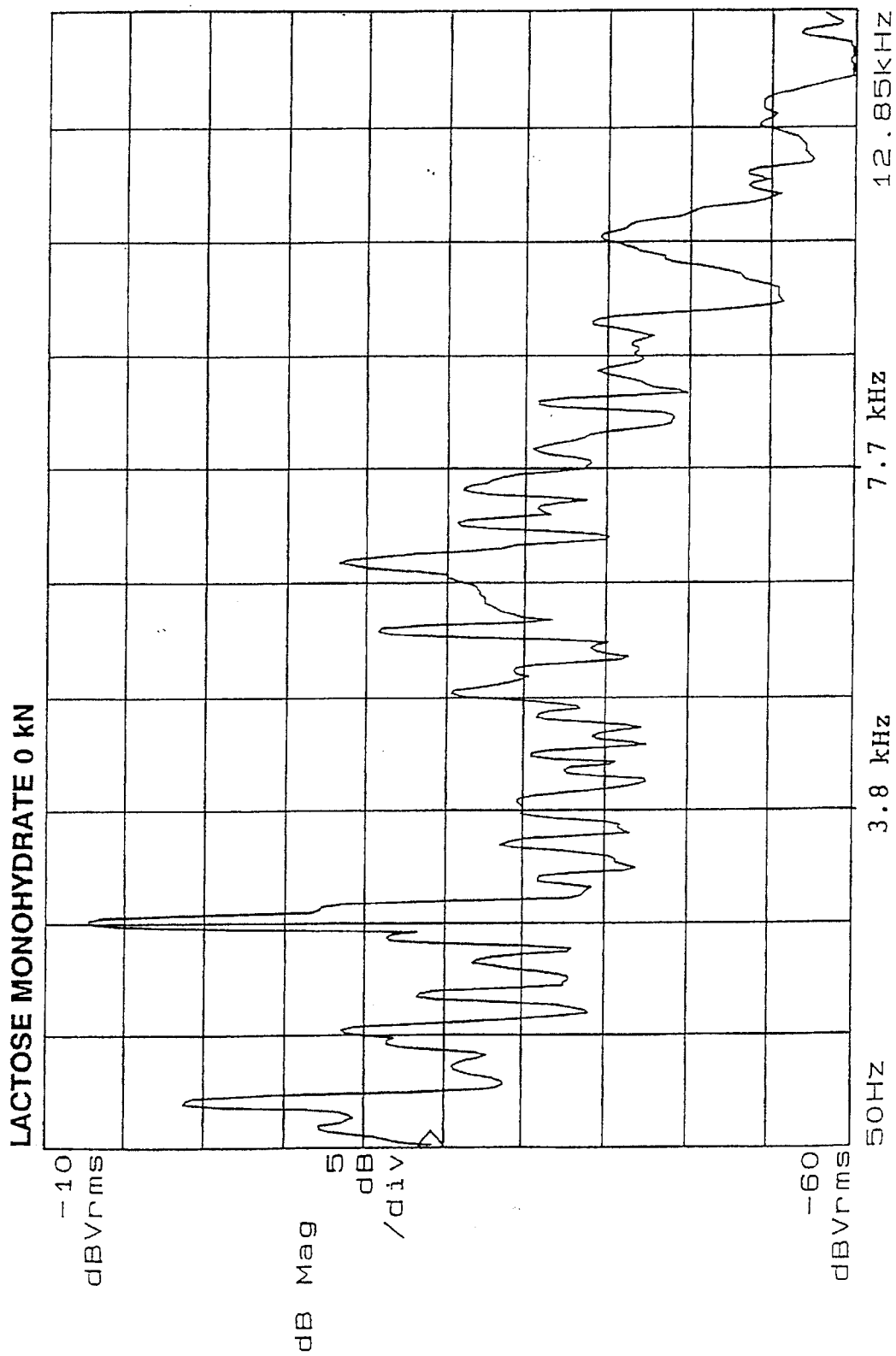
Figure 3B:
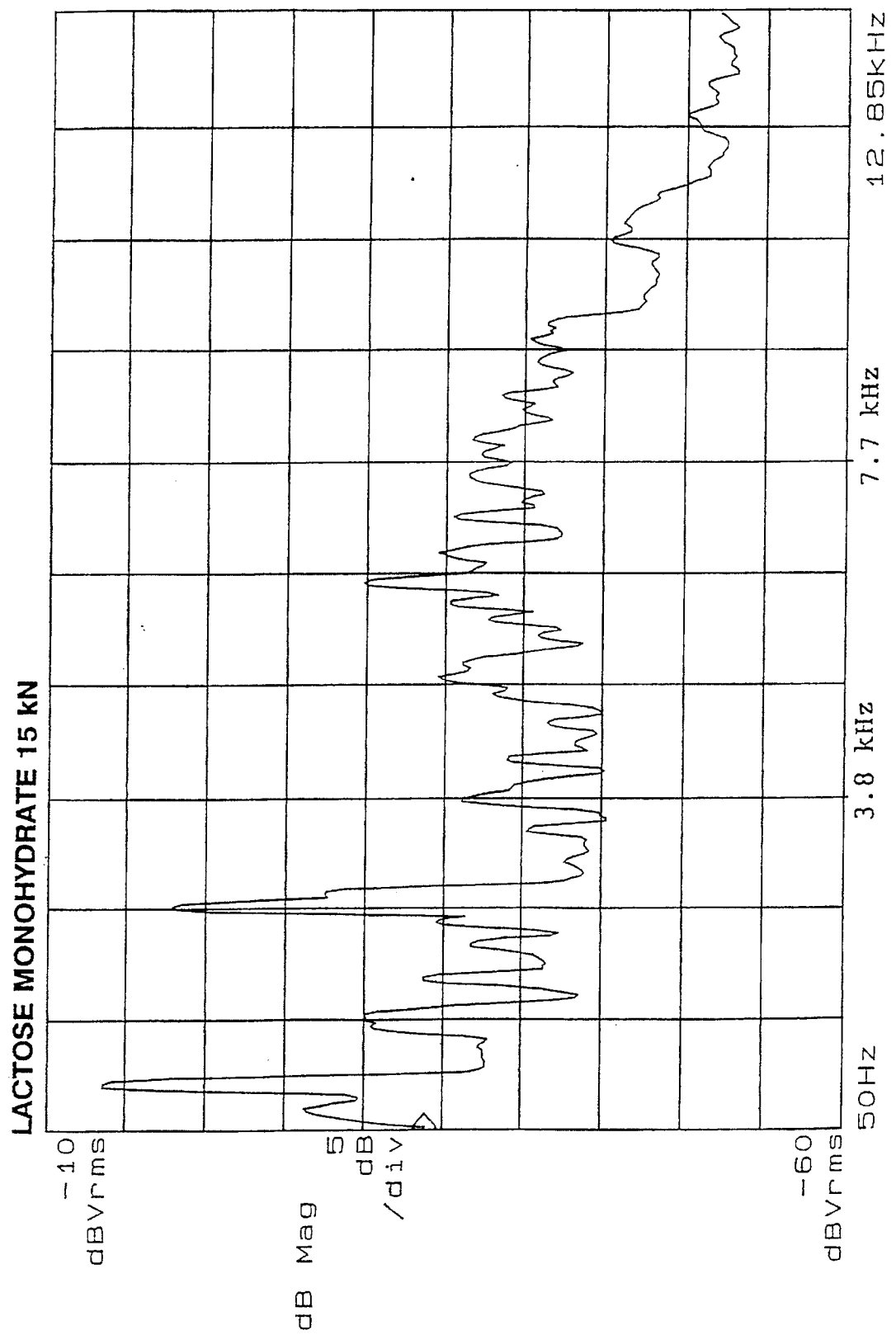
Figure 3C:
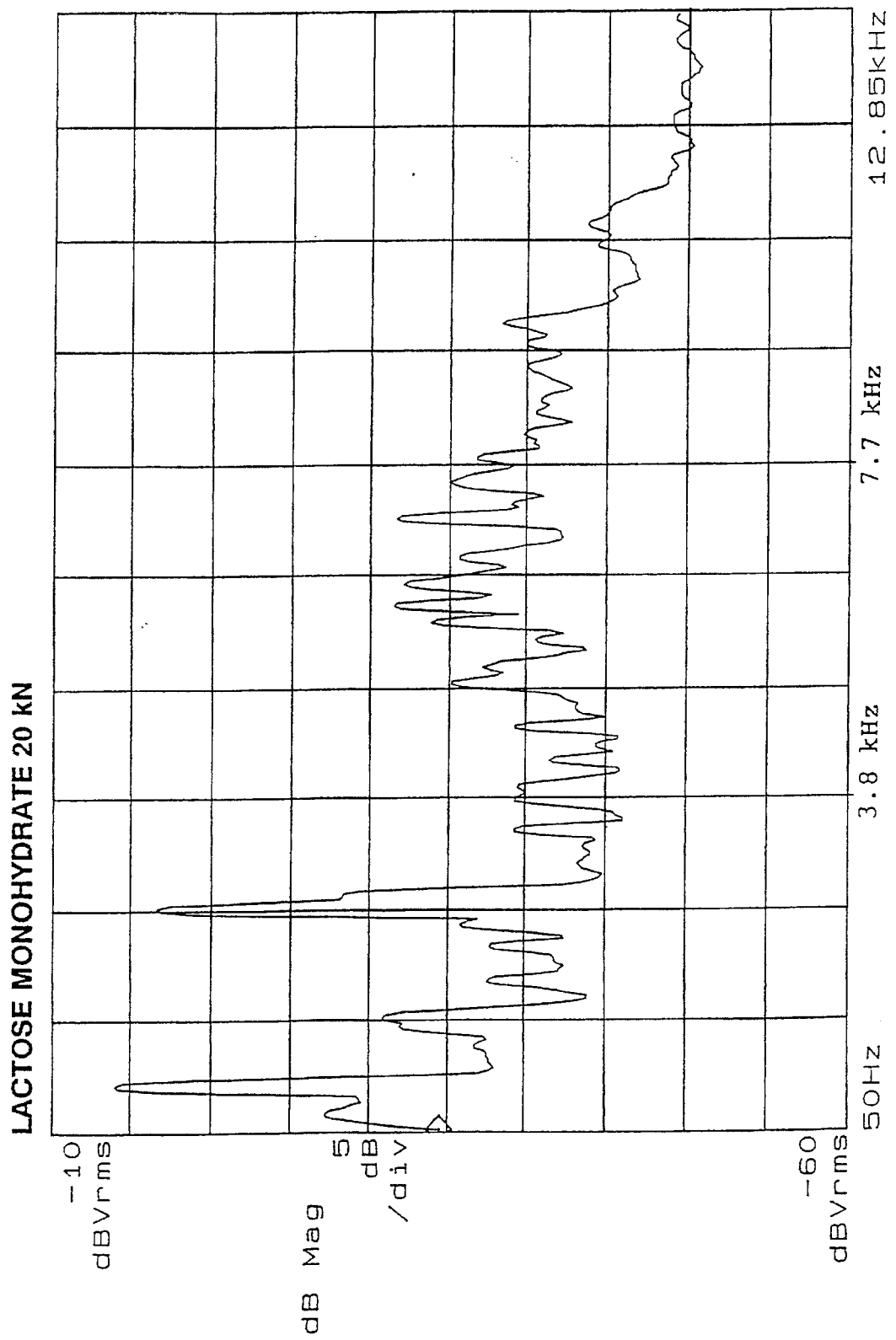
Figure 3E:
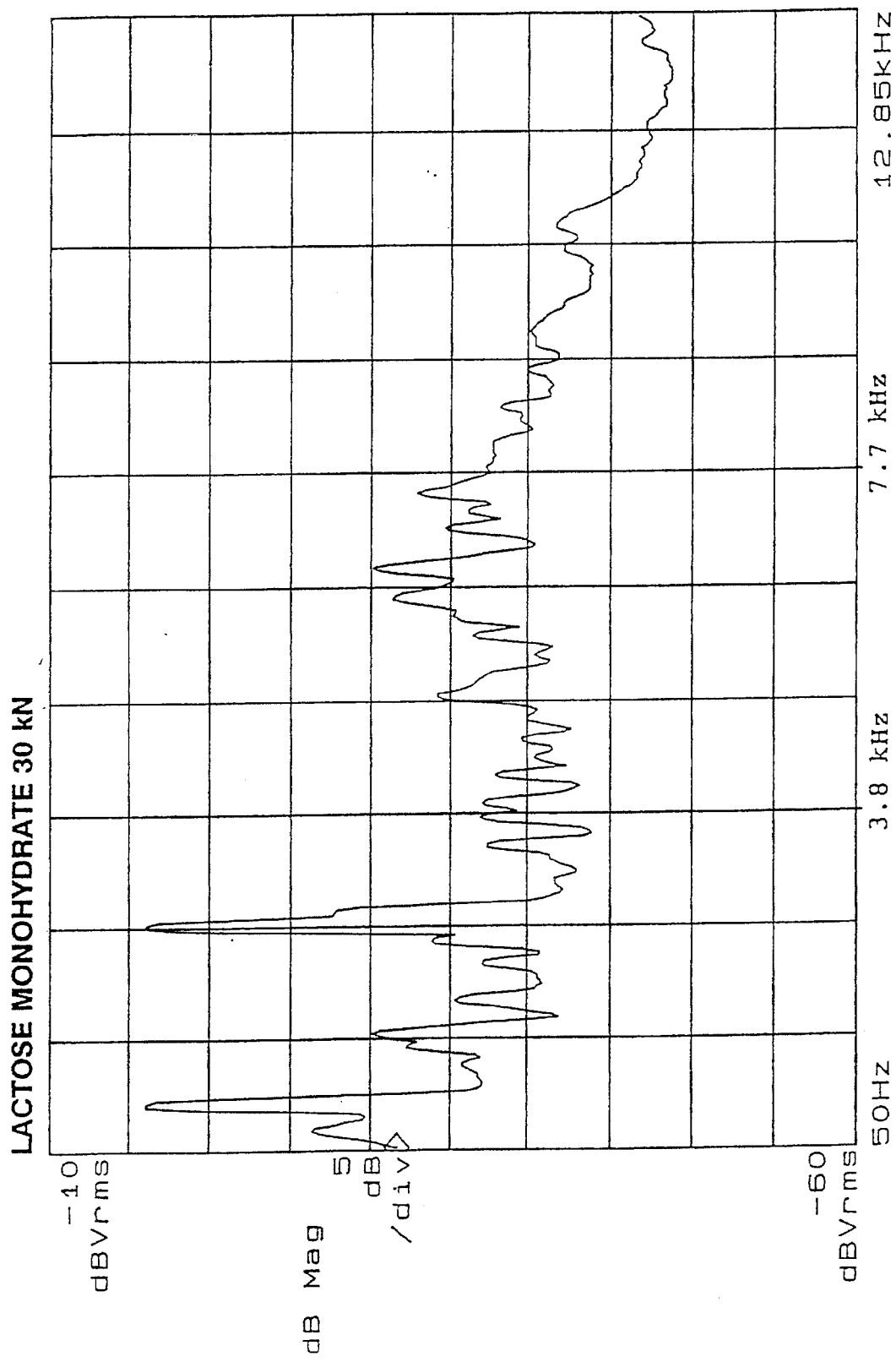

In FIG. 2, which shows the device used for the recording and further handling of the sound emission, reference number 20 signifies the microphone. Reference number 21 denotes the amplifier, number 22 the analog/digital converter, number 23 the frequency analyzer, and number 24 the monitor.

Table 1 shows the total acoustic power, or integrated intensity, of the total band and of the different narrower bands as regards the different substances studied and different compressive forces. The total band refers to 50 Hz–12.85 kHz; band 1 to 50 Hz–3.8 kHz; band II to 3.8–7.7 kHz and band III to 7.7–12.85 kHz. The substance-specific abbreviations have the following meanings: LM=lactose monohydrate, MC=microcrystalline cellulose, and MS=maize starch.

It was found that the sounds produced by the roller compactor formed distinct frequency peaks, whereas the sounds produced by the material being compacted appeared in wider bands. It was also found that the sounds produced by the machinery remained relatively well in the same place on the spectra while compressive forces varied.

The total spectrum (50 Hz–12.85 kHz) was divided into three bands based on the changes observed in the spectra, which were due to changes in compressive force. The band intensity [$dBV_{rms}$] was integrated in each band. The results are shown in Table I.

The first band band I, (50 Hz–3.8 kHz) included mainly the sounds produced by the machinery, and its integrated intensity represented a major part of the integrated intensity of the whole band.

Figure 4B:
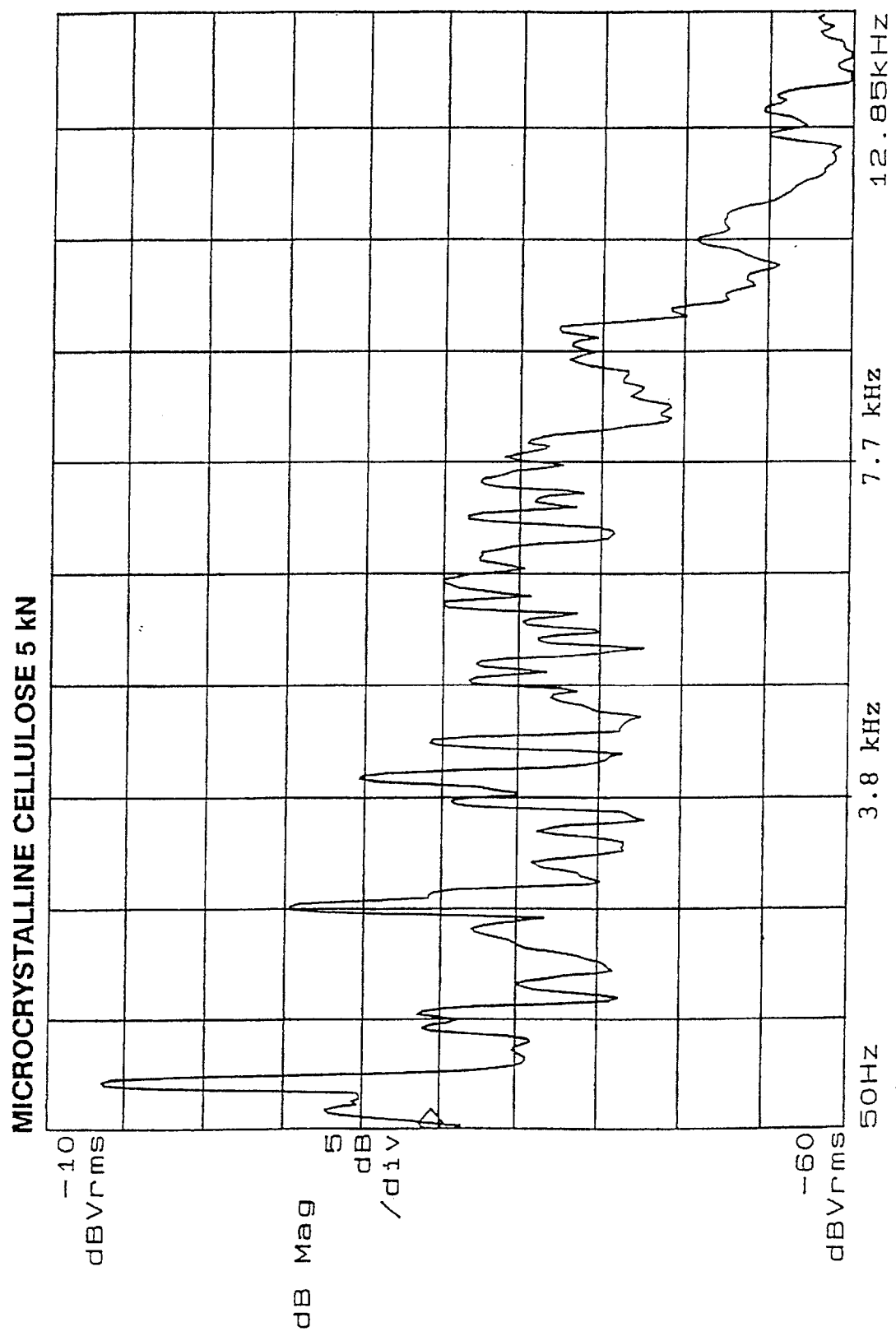
Figure 4C:
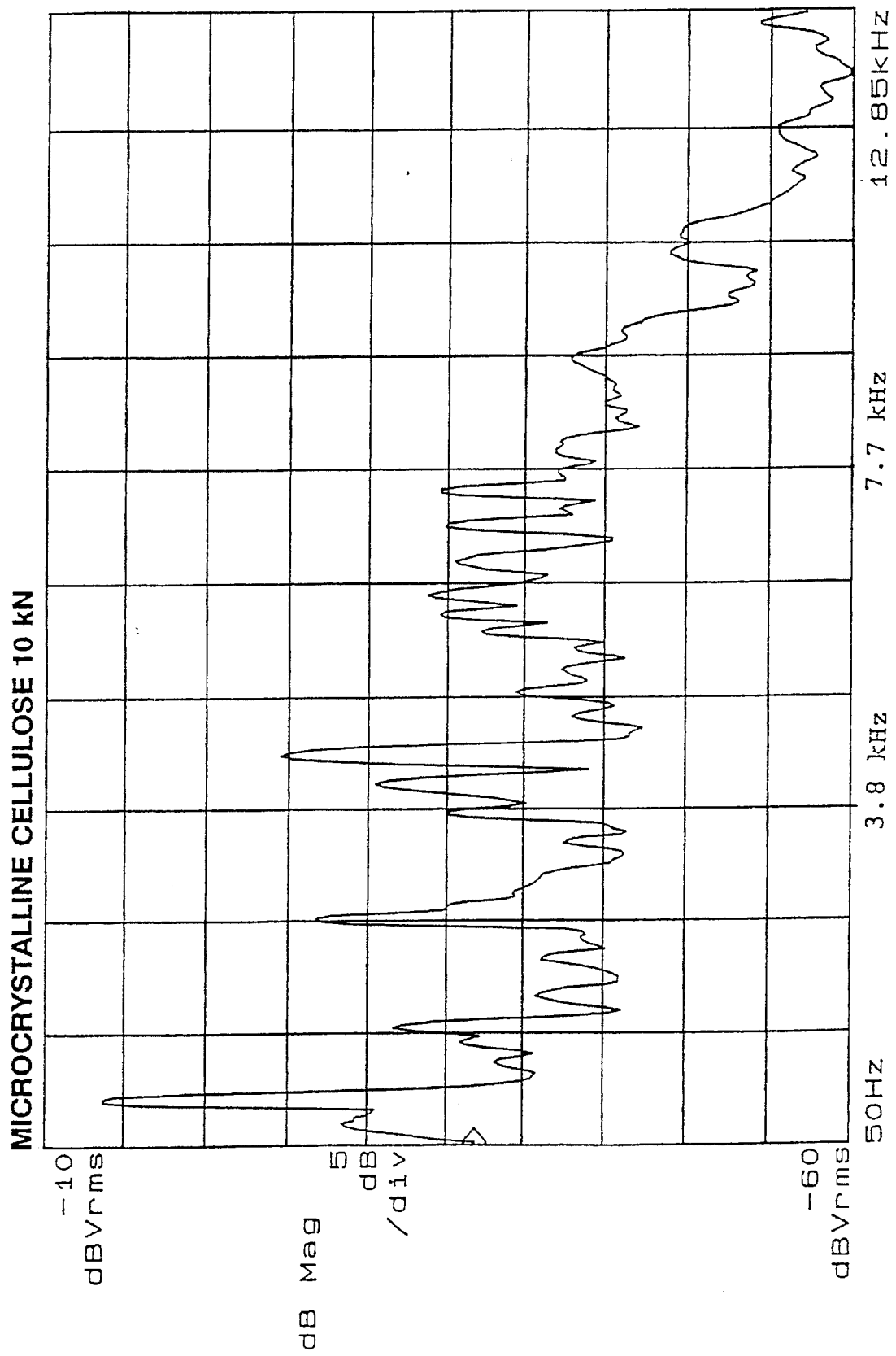

Generally speaking, there were few changes in the second band (band II) (3.8–7.7 kHz) when the compressive force was varied. However, when compacting microcrystalline cellulose, a few peaks were detected (FIGS. 4B, C, D, E and F) due to the feeder-compression screw of the compaction device rubbing on the cylinder wall. These sounds were also clearly audible.

Generally speaking, the powers of bands II and III were clearly weaker than the power of band I. Particularly the activity of band III had an effect on the compaction of powders.

The spectrum shows aspects which relate to the compressibility characteristics of the substances studied. When compressing maize starch with a compressive force of 5 kN (FIG. 5B), a significant increase in activity was detected in band I. The density of the powder was considerably lower than that of lactose monohydrate (FIGS. 3A–3F) and microcrystalline cellulose (FIGS. 4A-4I), and the loud squeaking produced by the compression of the powder could be clearly heard also during compaction. The sound disappeared as compressive force increased but appeared every time the machine was started. When recording signals, the compressive force was always allowed to stabilize before recording. Similar activity in band I was not detected with the other substances studied.

Figure 4D:
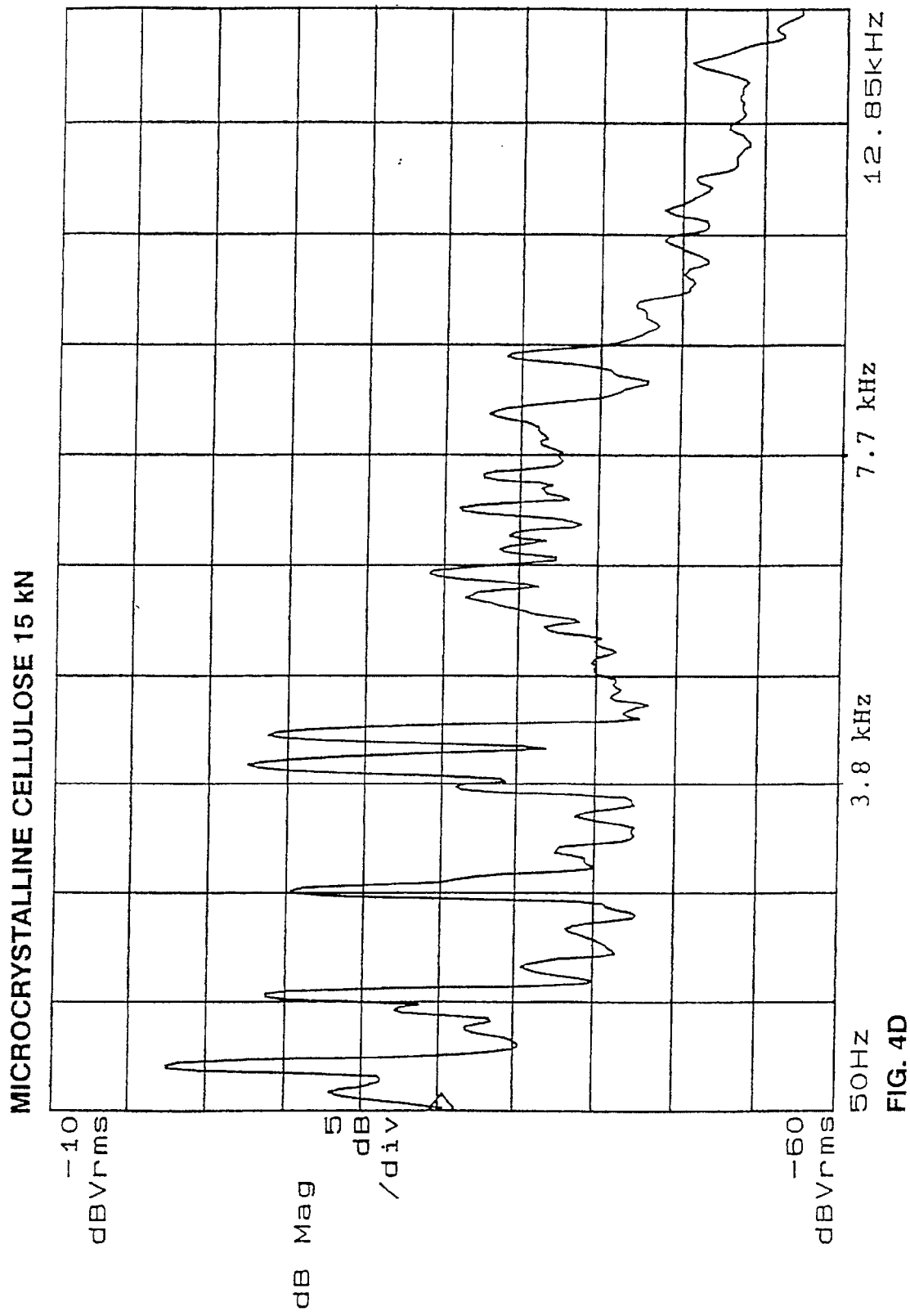
Figure 4E:
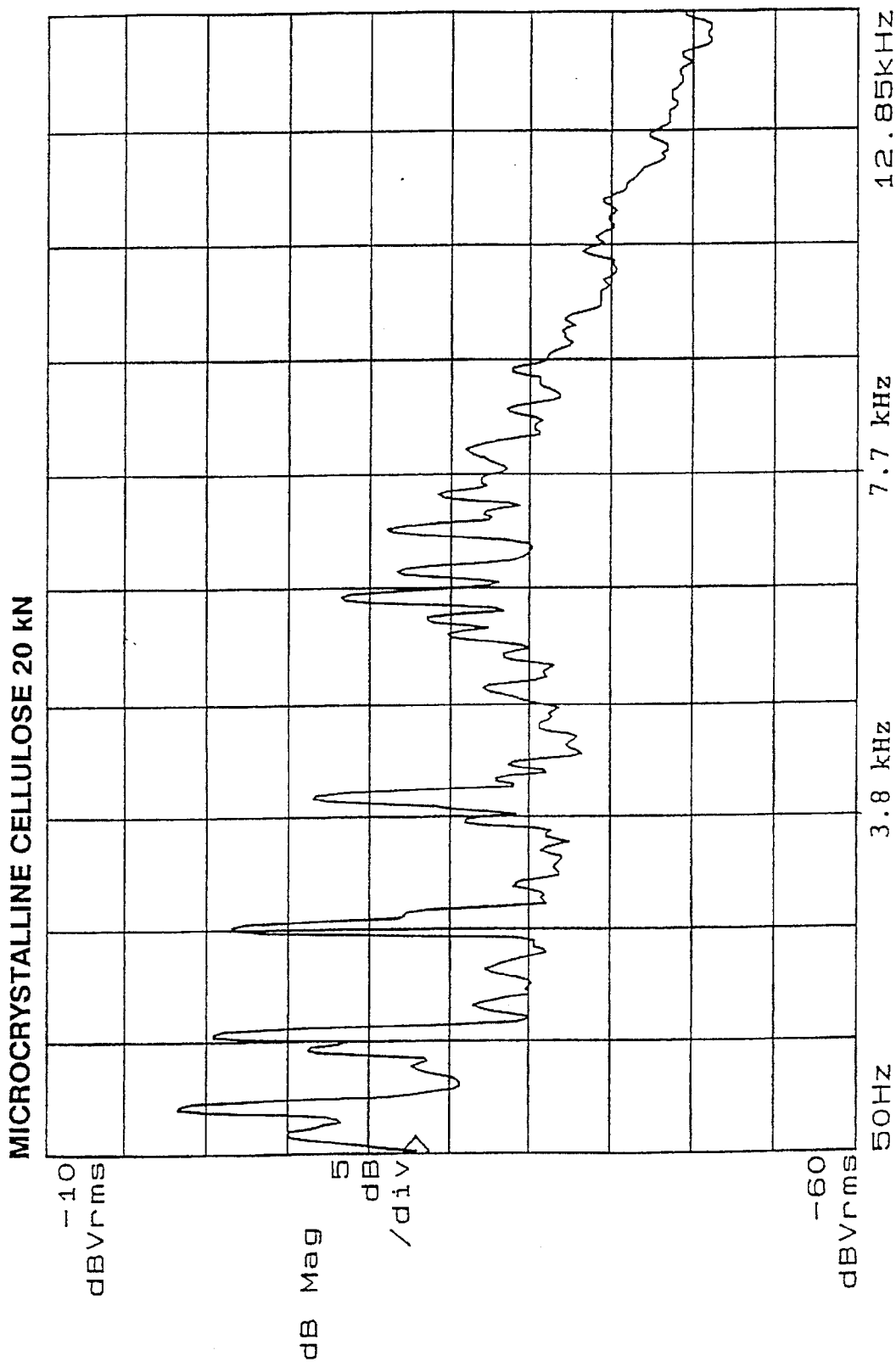
Figure 4F:
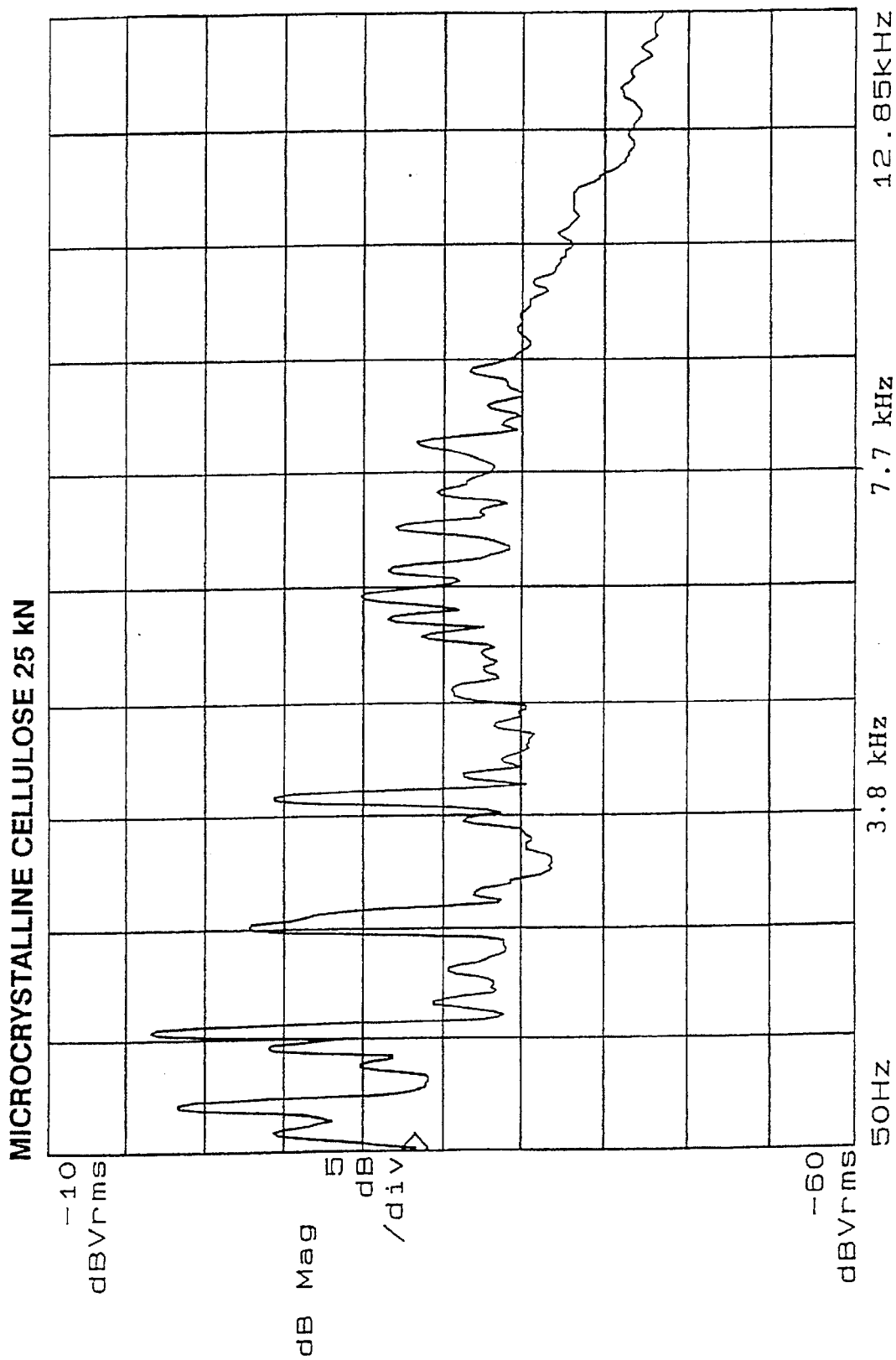
Figure 4G:
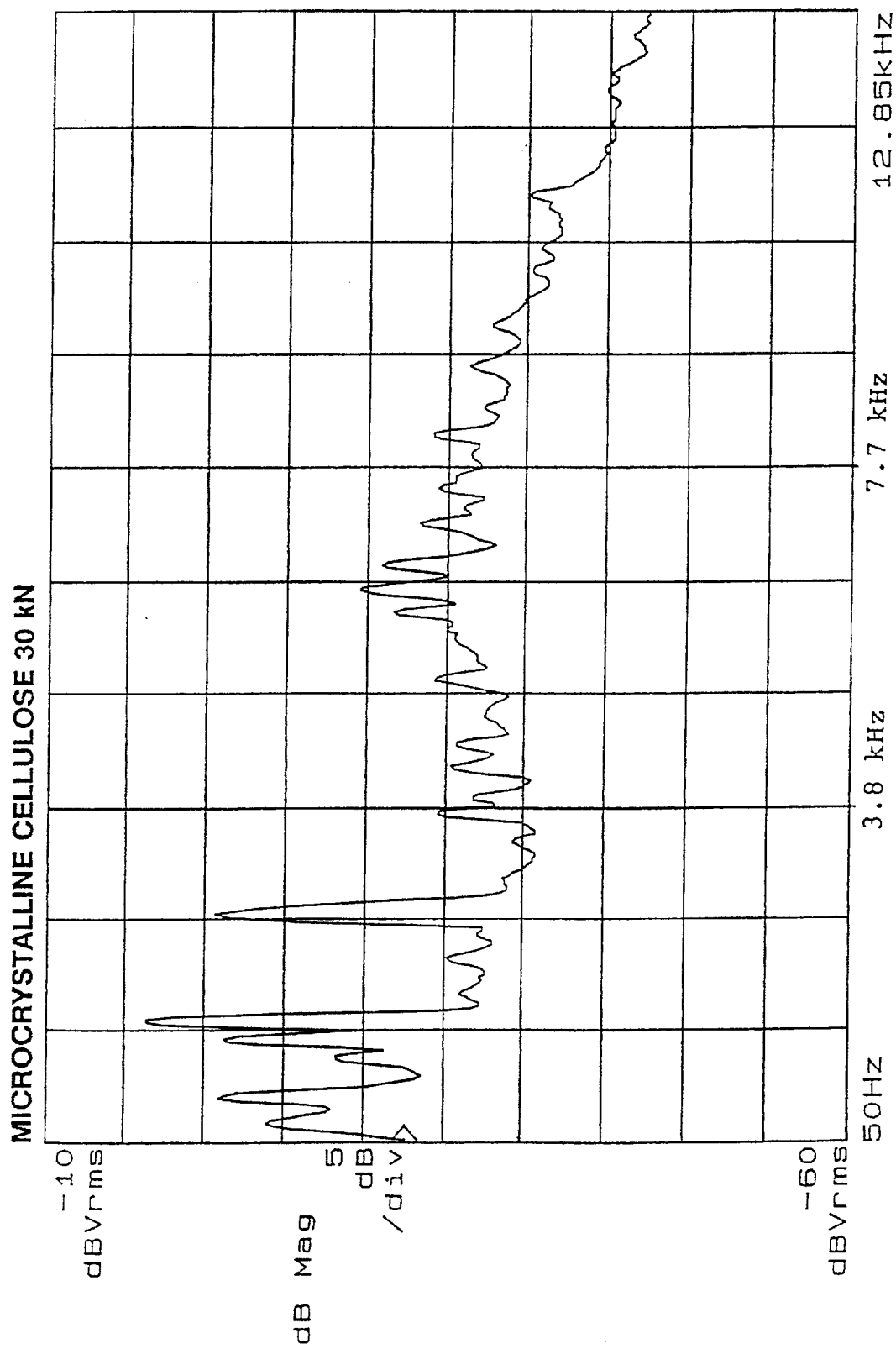
Figure 4H:
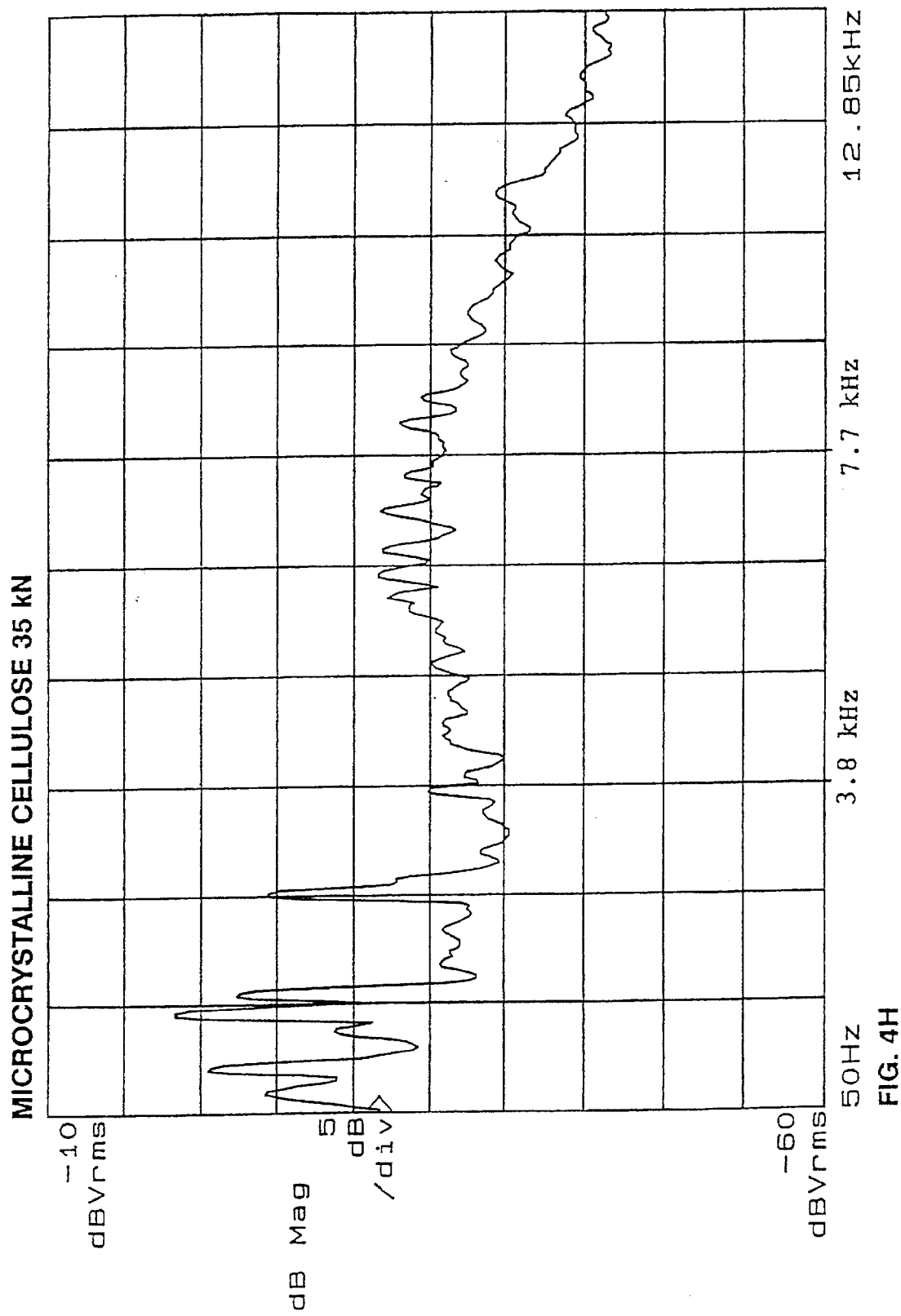
Figure 5B:
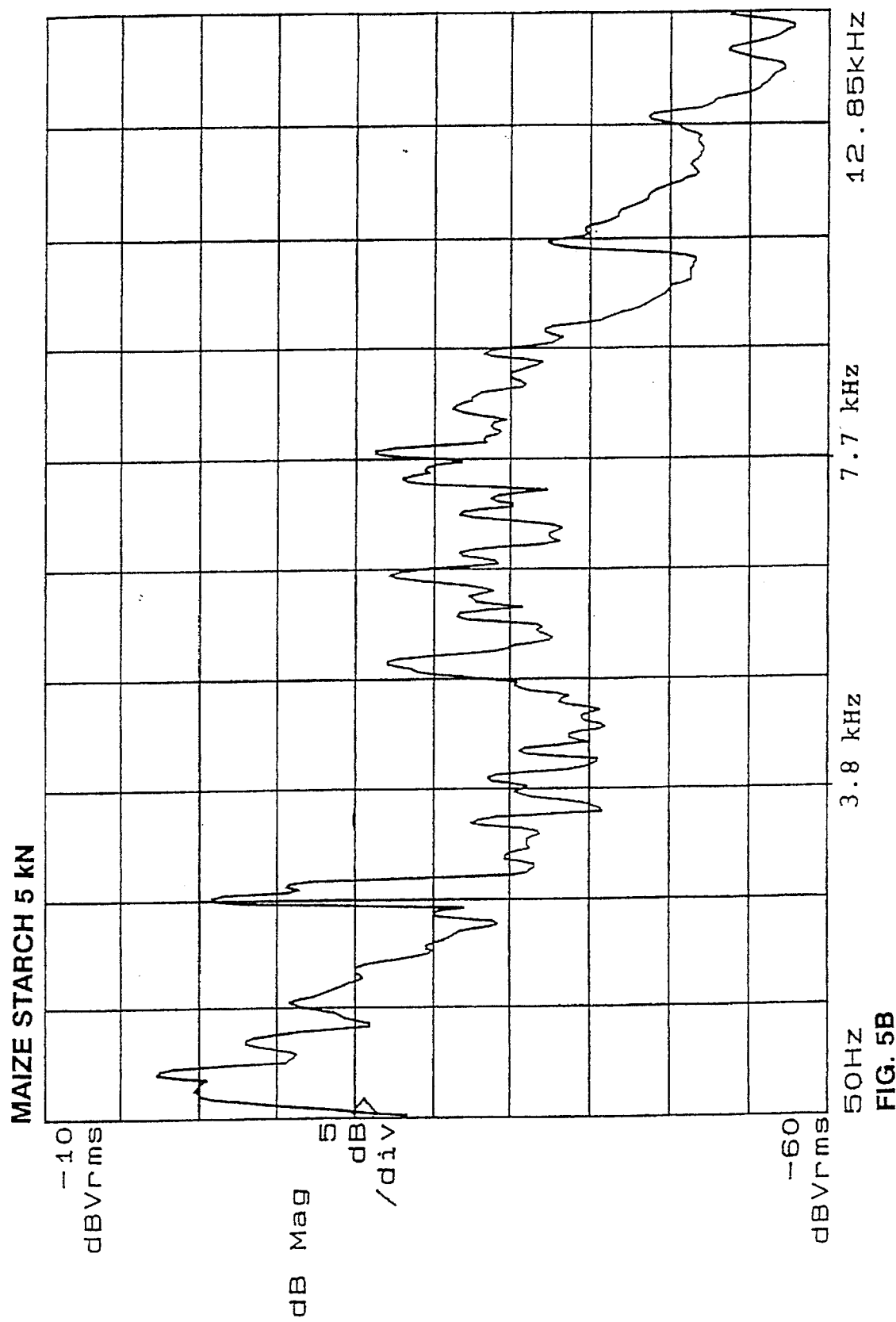
Figure 5C:
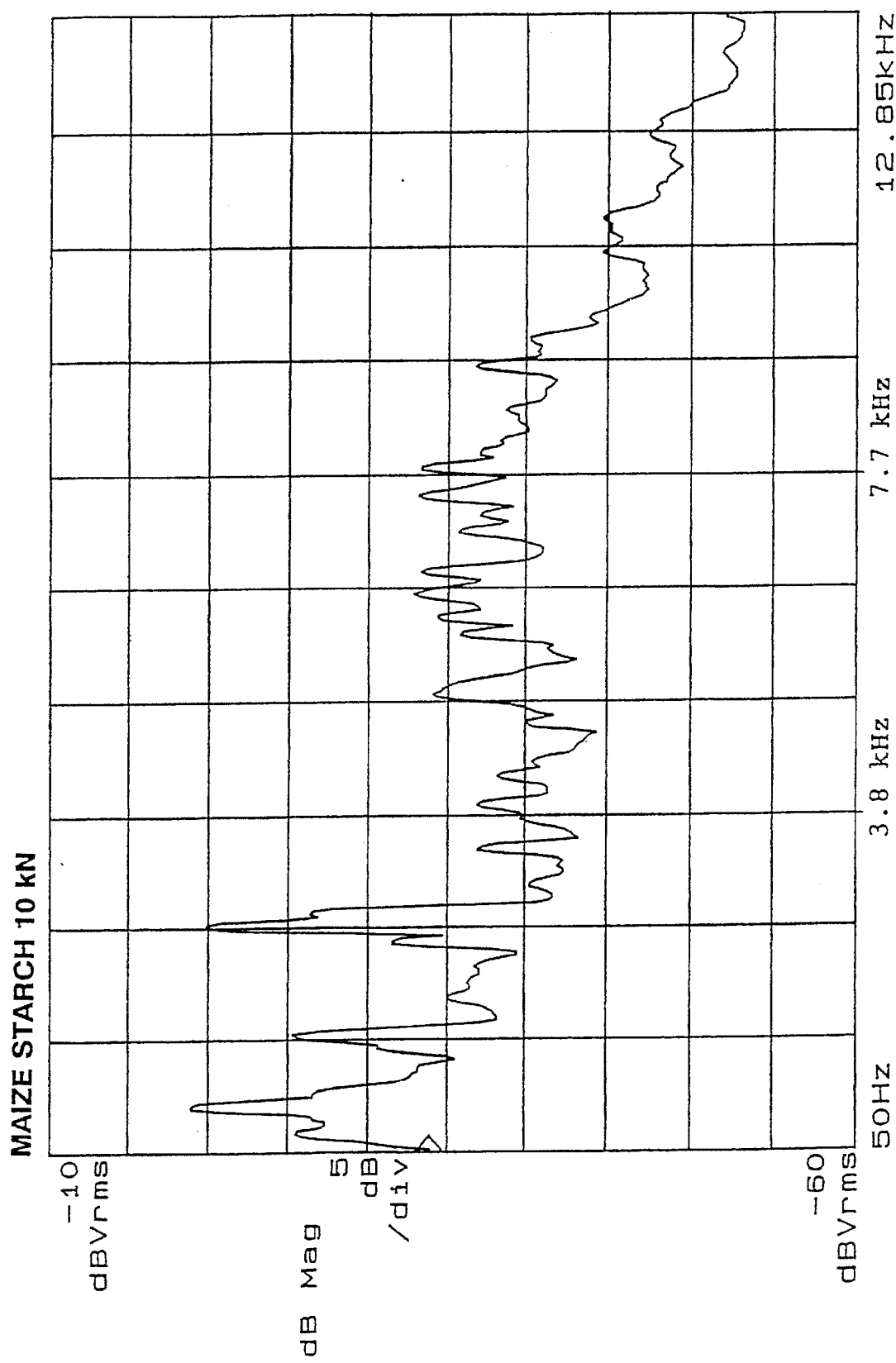
Figure 5D:
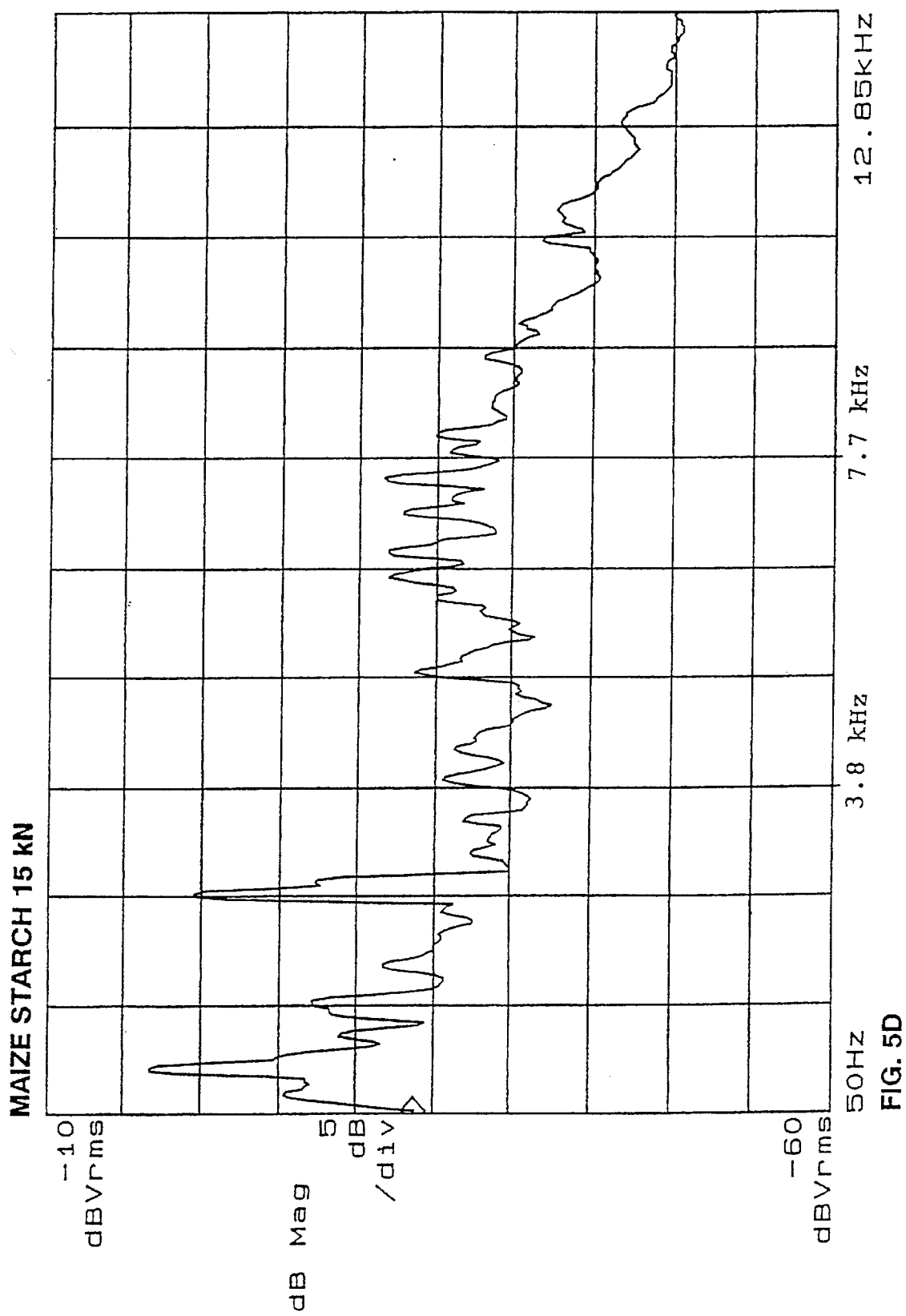
Figure 5E:
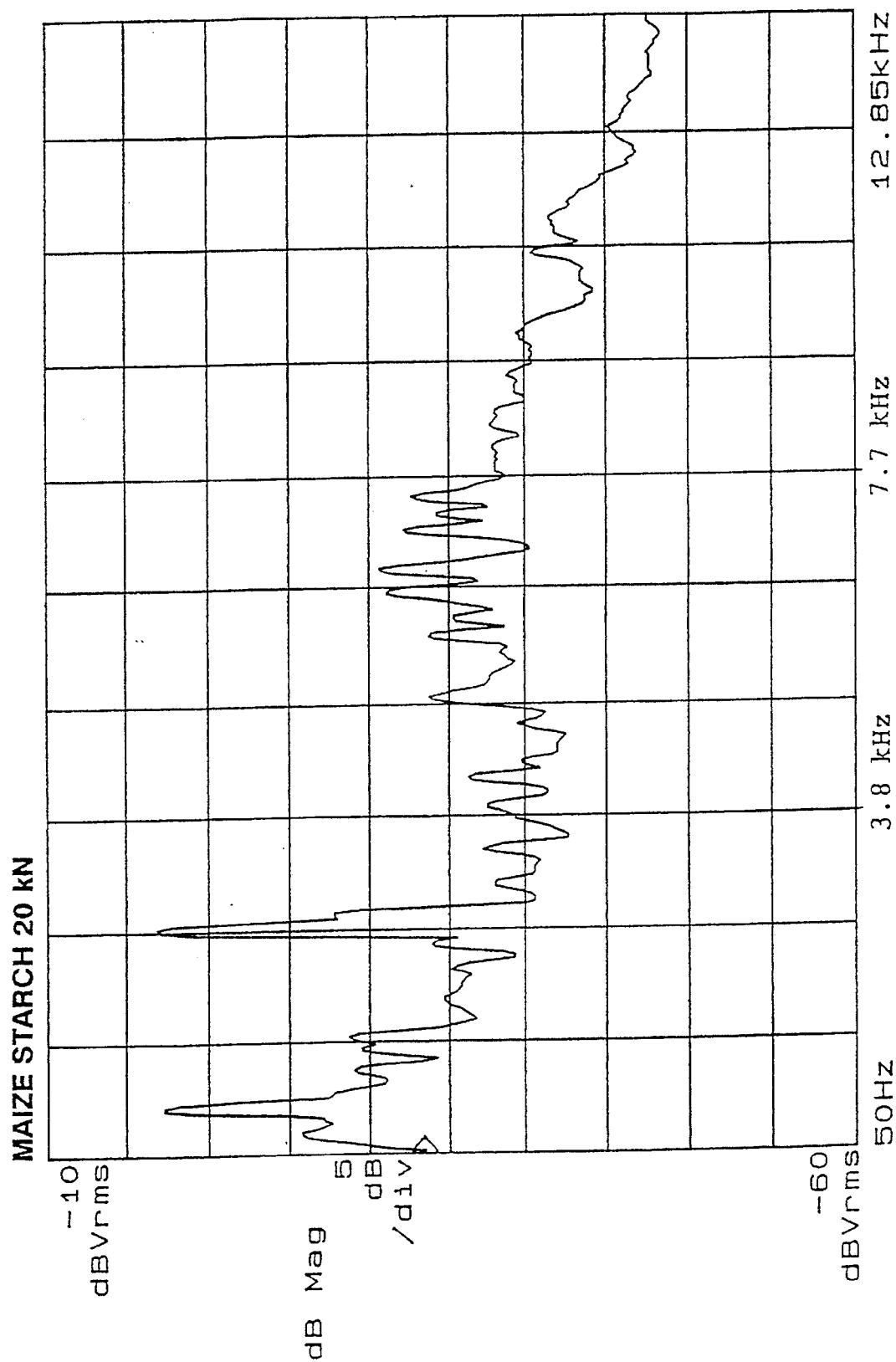
Figure 5F:
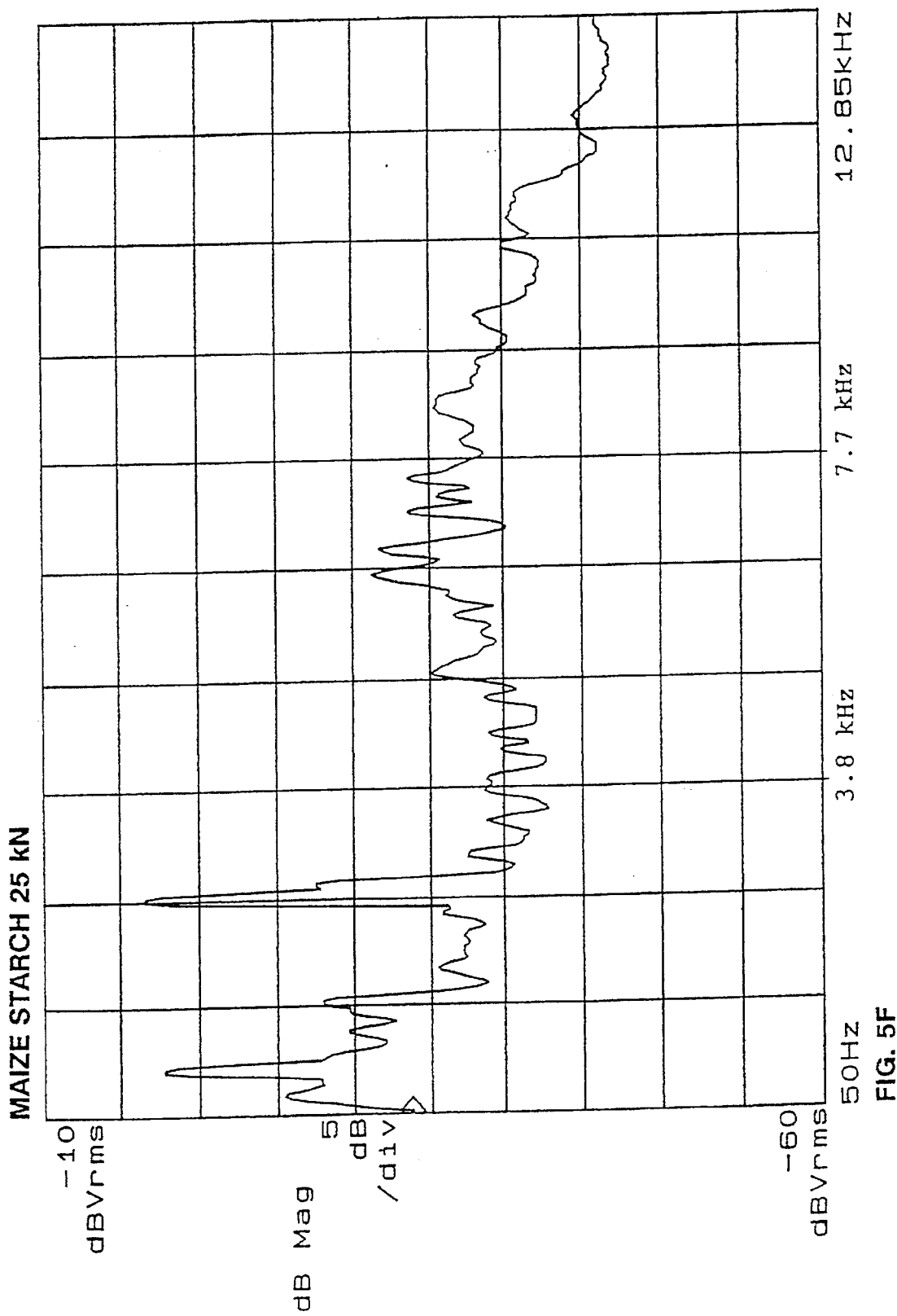
Figure 5G:
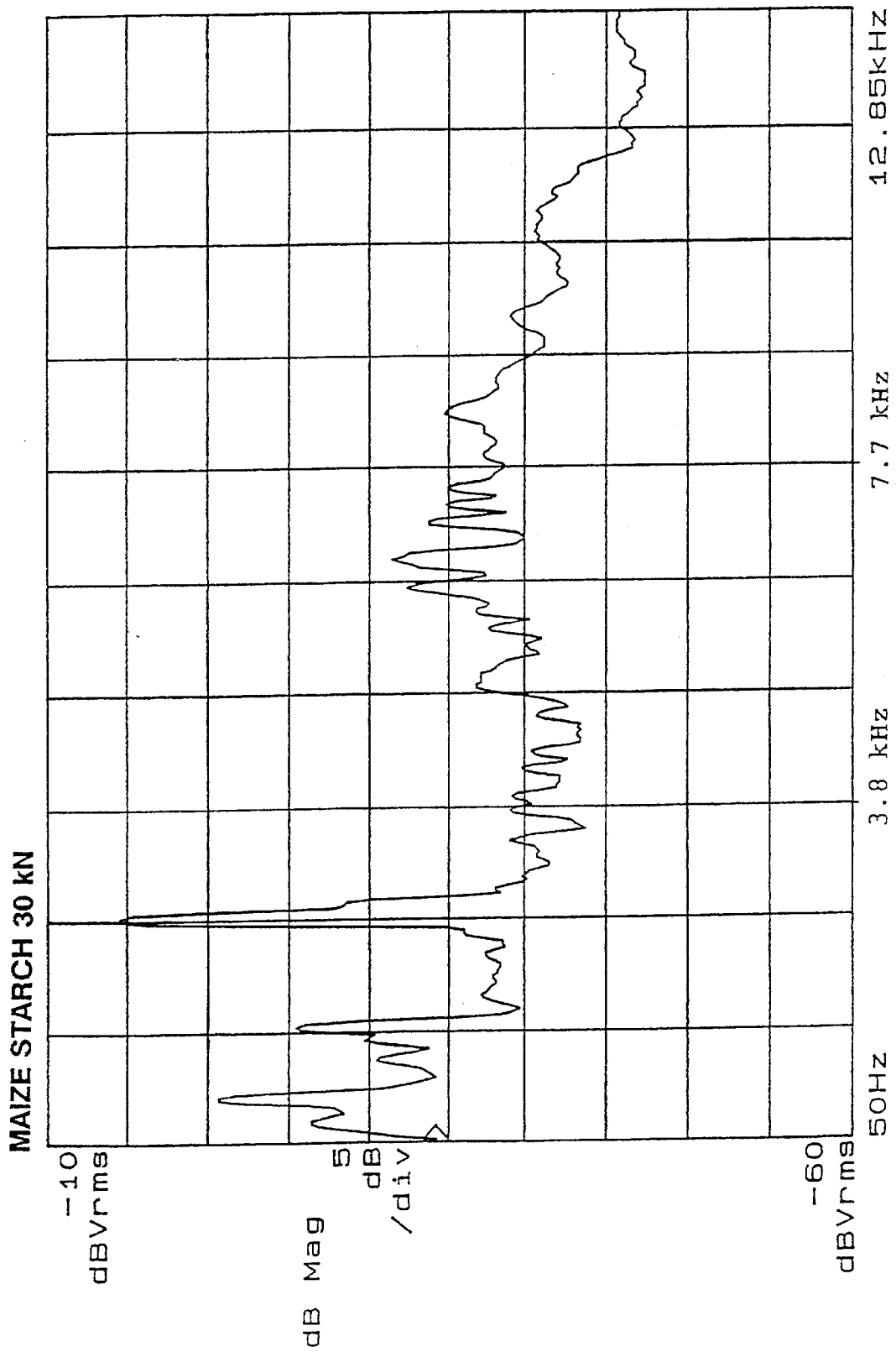
Figure 51:
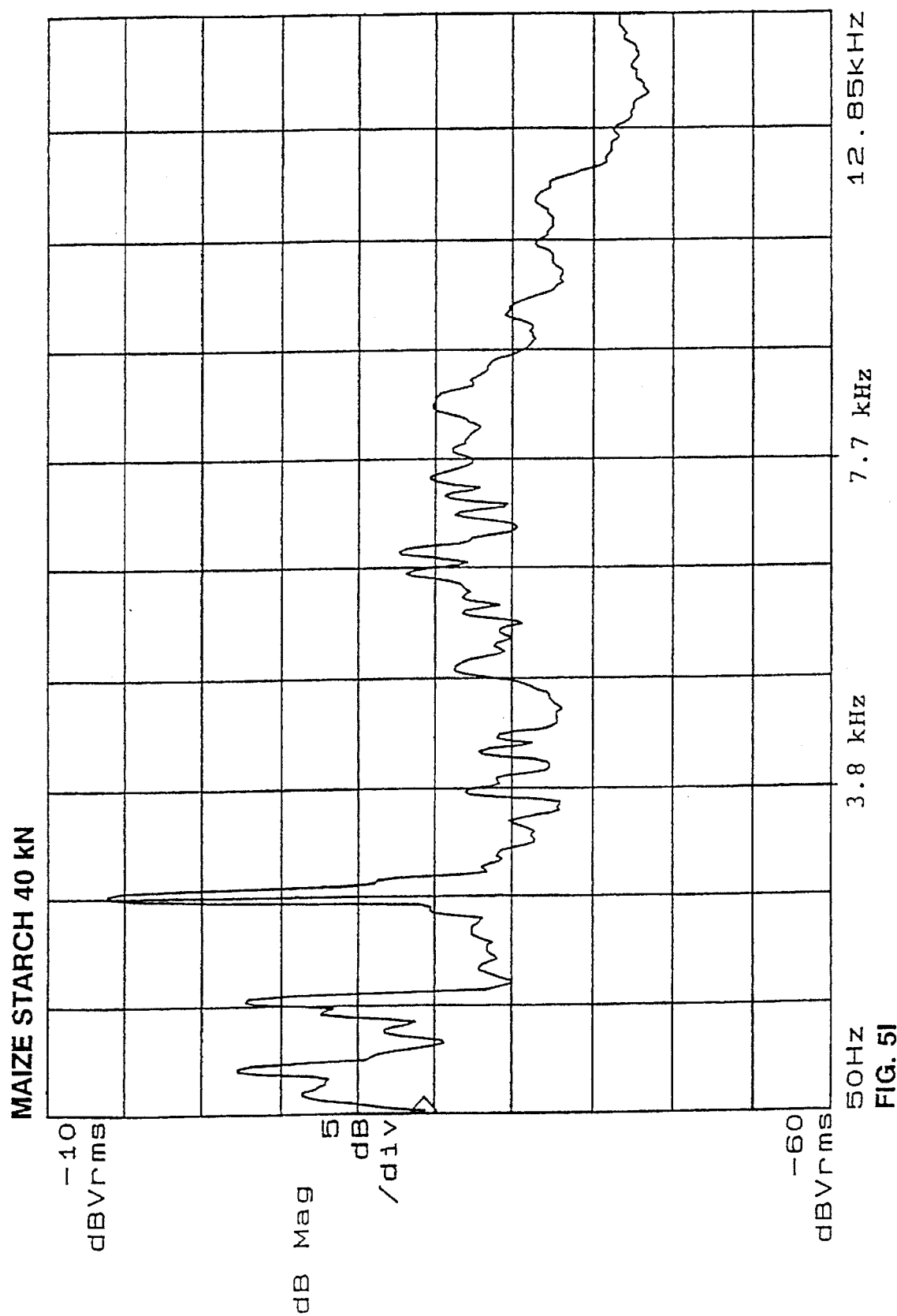
Figure 5K:
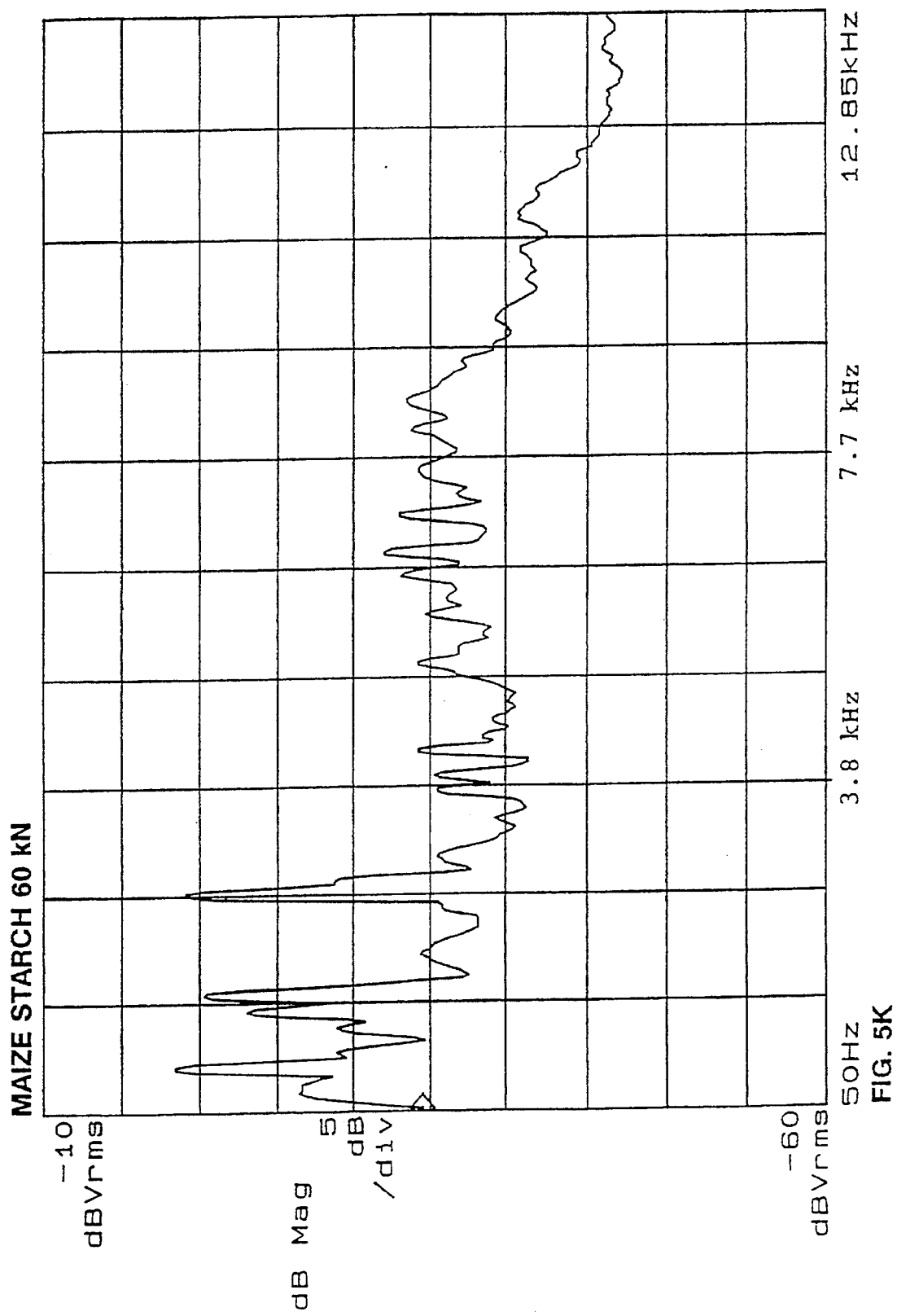

Generally speaking, the power of band I always decreases somewhat at the beginning because the powder dampens the machine-based sounds. At the same time, the activity of band III relating to the compression of the powder begins to increase. With microcrystalline cellulose this increase started at 15 kN (FIG. 4D). With lactose monohydrate 15 kN (FIG. 3B) was the smallest compressive force at which the material did not come through the compactor as powder. The power of band III had by then clearly increased. The power of band III increased with all substances when compressive force was increased, until it stabilized at the compressive force of 35 kN with lactose monohydrate (FIG. 3F) and at 40 kN with microcrystalline cellulose (FIG. 4I). Also with maize starch (FIGS. 5A-5K), changes were relatively small after 35 kN (FIGS. 5H-5K).

The third band, band III (7.7-12.85 kHz), was the most interesting band from the point of view of compaction. Particular attention should be paid to the growth spurts in band III with lactose monohydrate at 30 kN (FIG. 3E) and with microcrystalline cellulose at 20 kN (FIG. 4E), in which cases the compressed products were also better compacted. Maize starch also showed a growth spurt of some degree at 25 kN (FIG. 5F), but this could not be shown to be connected with compaction. Maize starch would presumably require a longer compression time for binding to take place. The number of connection points between hard starch particles would then have time to increase through plastic deformation.

In the third band it is possible to detect distinct peaks which provide information on certain phenomena. For example, in the case of microcrystalline cellulose, a peak appeared at compressive forces of 30, 35 and 40 kN (FIGS. 4G-I), and this may have described the capping phenomenon, in which case the compacted product broke lengthwise into two parts. Such distinct, accurately identifiable peaks make possible the quantitative analysis of such phenomena.

Figure 6:
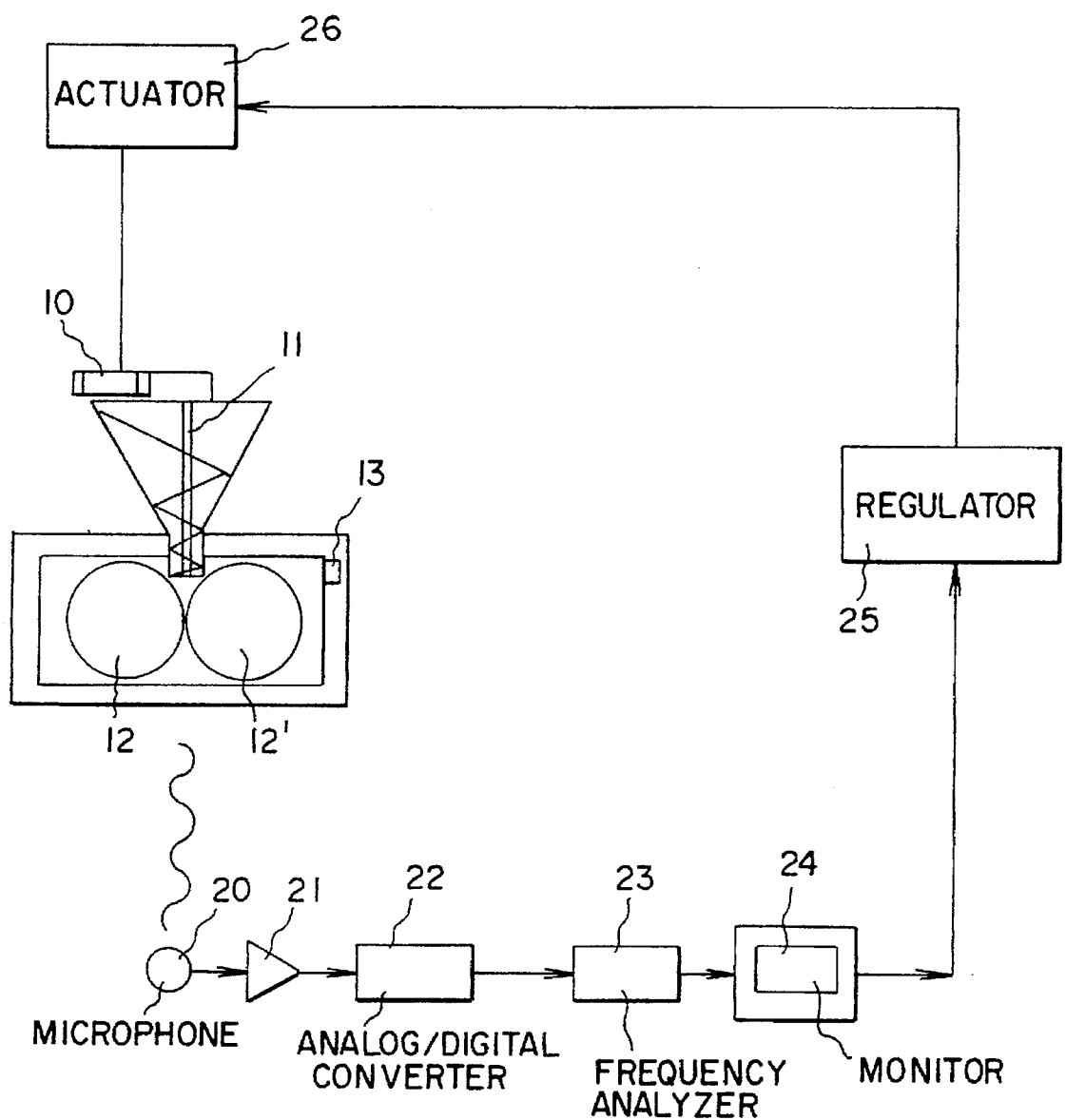
FIG. 6 shows one embodiment of the device relating to the invention for controlling the compaction process.

In FIG. 6—which shows one embodiment of the device relating to the invention for controlling the compaction process, and where the compaction takes place by means of the device relating to FIG. 1—sound emission is measured by means of a microphone 20, the said emission passing through an amplifier 21 to an analog/digital converter 22 and further through a frequency analyzer 23 to a monitor 24. The regulator 25 compares the value given by the monitor 24 with the set value of the standard spectrum and, on the basis of the observed deviation, gives a control signal to the actuator 26, which acts accordingly either increasing or decreasing compressive force.

The signal-noise ratio can be improved by using digital recording, especially at higher frequencies, and more sensitive microphones. Peak overlapping is another problem relating to quantitative analysis. The wide frequency range of the sounds in the third band may be due to wide particle size distribution in the powder. A third problem with quantitative analysis is that when compressive force is increased, the material flow between the rollers also increases. It is for this reason that possible sound effects are louder at greater compressive forces.

TABLE I

INTEGRATED BAND INTENSITY [dBV$_{rms}$]

| Compacted substance and force | Total band | Band I | Band II | Band III |
|---|---|---|---|---|
| LM 0 kN | −10.5 | −10.8 | −22.4 | −31.6 |
| LM 15 kN | −10.8 | −11.2 | −22.6 | −27.5 |
| LM 20 kN | −10.9 | −11.3 | −22.5 | −27.2 |
| LM 25 kN | −12.2 | −12.8 | −22.2 | −27.0 |
| LM 30 kN | −11.3 | −11.9 | −21.3 | −25.9 |
| LM 35 kN | −11.6 | −12.2 | −22.0 | −26.5 |
| MC 0 kN | −11.4 | −12.1 | −20.3 | −30.0 |
| MC 5 kN | −12.1 | −12.5 | −23.2 | −31.6 |
| MC 10 kN | −12.0 | −12.7 | −20.5 | −31.9 |
| MC 15 kN | −13.3 | −15.0 | −18.5 | −30.1 |
| MC 20 kN | −12.3 | −13.3 | −20.1 | −26.4 |
| MC 25 kN | −11.0 | −11.9 | −19.2 | −24.5 |
| MC 30 kN | −11.0 | −11.8 | −20.1 | −23.8 |
| MC 35 kN | −11.8 | −13.0 | −19.9 | −22.7 |
| MC 40 kN | −10.5 | −11.0 | −21.5 | −23.9 |
| MS 0 kN | −12.3 | −12.9 | −22.2 | −31.3 |
| MS 5 kN | −10.6 | −11.0 | −22.9 | −25.9 |
| MS 10 kN | −12.7 | −13.5 | −22.3 | −26.1 |
| MS 15 kN | −11.7 | −12.4 | −21.2 | −25.6 |
| MS 20 kN | −11.5 | −12.3 | −21.1 | −25.4 |
| MS 25 kN | −11.6 | −12.3 | −21.7 | −24.1 |
| MS 30 kN | −11.4 | −12.0 | −22.3 | −24.3 |
| MS 35 kN | −11.3 | −12.0 | −21.7 | −23.6 |
| MS 40 kN | −11.1 | −11.7 | −22.6 | −24.3 |
| MS 50 kN | −11.7 | −12.4 | −22.1 | −23.8 |
| MS 60 kN | −11.5 | −12.3 | −21.3 | −23.2 |

We claim:

1. A method for characterizing a compaction result of a powder during a compaction process, said method comprising the steps of:

a) measuring sound emission produced by the process by means of a sensor located in the vicinity of the process and transforming the sound emission into a frequency spectrum in which the sound intensity is presented as a function of frequency;

b) recording an intensity of a frequency band relating to the sound emission arising from the compaction of the powder and integrating the intensity of the frequency band by using a predetermined compressive force and noting the compaction result obtained; and c) changing the compressive force and repeating steps a) and b) to obtain the compaction result as a function of the intensity of the frequency band relating to the sound emission arising from compaction.

2. A method as claimed in claim 1 wherein the acoustic emission arising from the compressibility of the powder takes place essentially in the audible region.

3. A method for monitoring compaction of powder during a compaction process, said method comprising the steps of:

measuring the sound emission produced by the process by means of a sensor located in the vicinity of the process and transforming the sound emission into a frequency spectrum in which the sound intensity is shown as a function of frequency;

recording and integrating an intensity of the frequency band relating to the sound emission arising from the compaction of the powder, and comparing the sound intensity of the frequency band relating to the compaction of the powder with a corresponding sound intensity of a standard spectrum of the powder being compacted used as a normative value and recording any deviation therebetween; and recording and integrating an intensity of the frequency band relating to the sound emission caused by compaction equipment used in the process, and comparing the sound intensity of the frequency band relating to the functioning of the compaction equipment with a corresponding sound intensity of a standard spectrum used as a normative value and recording any deviation therebetween.

4. A method as claimed in claim 2 wherein a change is made in the compaction process on the basis of a recorded deviation.

5. A method as claimed in claim 4, wherein the compacted material is directed along a route deviating from the normal one and the process is possibly discontinued.

6. A method as claimed in claim 4, wherein if the sound intensity of a band sensitive to powder compaction deviates from the set base range of the corresponding standard spectrum, the compressive force of the compaction device is changed so that the sound intensity of the band sensitive to powder compaction is directed back into the normative range.

7. A method as claimed in claim 3, wherein the acoustic emission arising from the compressibility of the powder takes place essentially in the audible region.

8. A method as claimed in claim 2, wherein a change is made in the compaction process on the basis of a recorded deviation.

9. A method as claimed in claim 7, wherein a change is made in the compaction process on the basis of a recorded deviation.

10. A device for compacting powder, comprising:
means for compacting powder;
a microphone disposed proximate to said powder compacting means;
an amplifier connected to said microphone;
an analog/digital converter connected to said amplifier;
a frequency analyzer connected to said converter;
a monitor connected to said analyzer;
means for detecting deviation between a value from said monitor and a set value of a standard spectrum and generating a control signal on the basis of the detected deviation; and
means for adjusting said powder compacting means to vary a compressive force applied to powder during compaction, said adjusting means being activated by said control signal generated by said detecting means.

* * * * *